(12) United States Patent
Meng et al.

(10) Patent No.: US 9,585,951 B2
(45) Date of Patent: *Mar. 7, 2017

(54) LIVE ATTENUATED CHIMERIC PORCINE CIRCOVIRUS VACCINE

(75) Inventors: Xiang-Jin Meng, Blacksburg, VA (US); Nathan M. Beach, Blacksburg, VA (US); Sheela Ramamoorthy, Tifton, GA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/049,364

(22) Filed: Mar. 16, 2011

(65) Prior Publication Data
US 2011/0280905 A1    Nov. 17, 2011

Related U.S. Application Data

(60) Provisional application No. 61/314,362, filed on Mar. 16, 2010.

(51) Int. Cl.
| | |
|---|---|
| A61K 39/12 | (2006.01) |
| C12N 7/00 | (2006.01) |
| C12N 15/63 | (2006.01) |
| A61P 31/12 | (2006.01) |
| A61P 31/20 | (2006.01) |
| A61K 39/00 | (2006.01) |

(52) U.S. Cl.
CPC ............... *A61K 39/12* (2013.01); *C12N 7/00* (2013.01); *A61K 2039/5252* (2013.01); *A61K 2039/5254* (2013.01); *A61K 2039/552* (2013.01); *C12N 2750/10022* (2013.01); *C12N 2750/10034* (2013.01); *C12N 2750/10051* (2013.01); *C12N 2750/10062* (2013.01)

(58) Field of Classification Search
CPC .................... A61K 39/12; C12N 7/045; C12N 2750/10022; C07K 14/005
USPC ........................................................ 424/204
See application file for complete search history.

(56) References Cited

U.S. PATENT DOCUMENTS

| | | | |
|---|---|---|---|
| 7,276,353 | B2 | 10/2007 | Meng et al. |
| 7,279,166 | B2 | 10/2007 | Meng et al. |
| 7,575,752 | B2 | 8/2009 | Meng et al. |
| 2009/0017064 | A1* | 1/2009 | Wu et al. .................. 424/205.1 |
| 2009/0162398 | A1 | 6/2009 | Wu |
| 2009/0221018 | A1 | 9/2009 | Kwang et al. |
| 2010/0055122 | A1 | 3/2010 | Meng et al. |
| 2011/0305725 | A1 | 12/2011 | Wu |

FOREIGN PATENT DOCUMENTS

| | | |
|---|---|---|
| CN | 1693455 A | 11/2005 |
| WO | 2009085912 A1 | 7/2009 |

OTHER PUBLICATIONS

Fort et al. Porcine circovirus type 2 (PCV2) vaccination of conventional pigs prevents viremia against PCV2 isolates of different genotypes and geographic origins, 2008, Vaccine, 26:1063-1071.*
Opriessnig et al., "Differences in virulence among porcine circovirus type 2 isolates are unrelated to cluster type 2a or 2b and prior infection provides heterologous protection", 2008, J Gen Virol, 89(10):2482-2491.*
Fenaux et al. "A chimeric porcine circovirus (PCV) with the immunogenic capsid gene of the pathogenic pcv type 2 (PCV2) cloned into the genomic backbone of the nonpathogenic PCV1 induces protective immunity against PCV2 infection in pigs", 2004, Journal of Virology, 78(12):6297-6303.*
Tischer, I. et al., "Characterization of Papovavirus-and Picornavirus-like Particles in Permanent Pig Kidney Cell Lines"; Zbl. Bakt. Hyg., I.Abt. Orig., 1974, pp. 153-167, vol. 226.
Tischer, I. et al., "A Very Small Porcine Virus with Circular Single-Stranded DNA"; Nature, Macmillan Journals, 1982, pp. 64-66, vol. 295.
Todd, D. et al., C. M. Fauquet et al (ed.), "Circoviridae"; Elsevier Academic Press, 2005, pp. 327-334.
Tomas, A. et al., A Meta-Analysis on Experimental Infections with Porcine Circovirus Type 2 (PCV2); Veterinary Microbiology, 2008, pp. 260-273, vol. 132.
Wang, F. et al., "Genetic Variation Analysis of Chinese Strains of Porcine Circovirus Type 2"; Virus Research, 2009, pp. 151-156, vol. 145.
Wiederkehr, D. D. et al., "A New Emerging Genotype Subgroup within PCV-2b Dominates the PMWS Epizooty in Switzerland"; Veterinary Microbiology, 2009, pp. 27-35, vol. 136.
Fenaux, M., et al., A Chimeric Porcine Circovirus (PCV) with the Immunigenic Capsid Gene of the Pathogenic PCV Type 2 (PCV2) Cloned into the Genomic Backbone of the Nonpathogenic PCV1 Induces Protective Immuniity against PCV2 Infention in Pigs, Journal of Virology, Jun. 2004, p. 6297-6303, vol. 78, No. 12, American Society for Microbiology.
Fenaux, M., et al., Immunigenicity and Pathogenicity of Chimeric Infectious DNA Clones of Pathogenic Porcine Circovirus Type 2 (PCV2) and Nonpathogenic PCV1 in Weanling Pigs, Journal of Virology, 2003, pp. 11232-11243, vol. 77 No. 20, American Society for Microbiology.

(Continued)

*Primary Examiner* — Janet L Andres
*Assistant Examiner* — Barry A Chestnut
(74) *Attorney, Agent, or Firm* — Anne M. Rosenblum

(57) ABSTRACT

The present invention provides a novel chimeric porcine circovirus infectious DNA clone and live attenuated chimeric virus with the PCV2, preferably of subtype PCV2b, capsid gene integrated into a non-pathogenic PCV1 virus genome. In a particular embodiment, the PCV2 capids gene is of subtype PCV2b, the predominant subtype circulating in pigs worldwide. The attenuated chimeric virus, designated PCV1-2b, effectively protects pigs from PCV2b challenges, and can be used as a live vaccine, as well as an inactivated (killed) vaccine, that provides protection and cross protection against PCV2b and PCV2a subtypes infection. The live attenuated vaccine of the present invention is also effective protecting pigs from porcine circovirus-associated disease (PCVAD).

14 Claims, 7 Drawing Sheets

(56) References Cited

OTHER PUBLICATIONS

Figure 1:
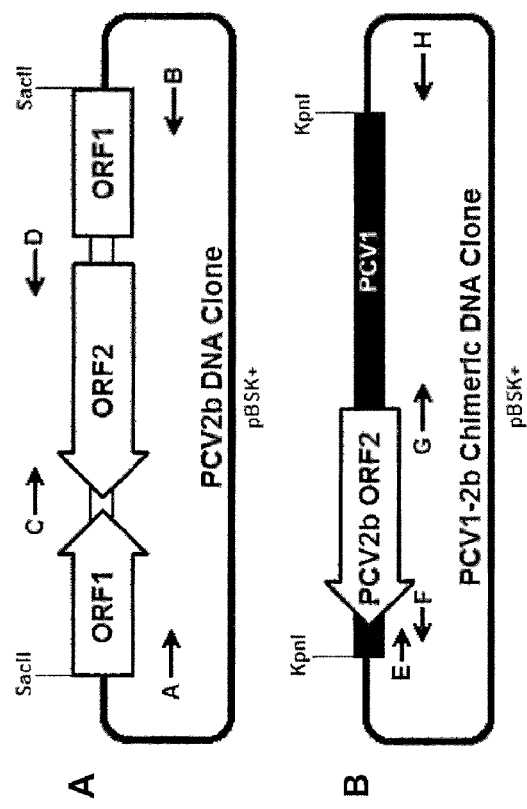

Horlen, M., Kyle, et al., A Cluster of Farms Experiencing Severe Porcine Circovirus Associated Disease, Clinical Features and Associations with the PCV2b Genotype, Journal of Swine Health and Production, 2007, pp. 270-278, vol. 15, No. 5.
Allan, G. et al., "Reproduction of Postweaning Multisystemic Wasting Syndrome in Pigs Experimentally Inoculated with a Swedish Porcine Circovirus 2 Isolate", Journal of Veterinary Diagnostic Investigation, 2003, pp. 553-560, vol. 15.
Allan, G.M. and J.A. Ellis, "Porcine Circoviruses: A Review"; Journal of Veterinary Diagnostic Investigation, 2000, pp. 3-14, vol. 12.
Allan, G. M. et al., "Experimental Infection of Colostrum Deprived Piglets with Porcine Circovirus 2 (PCV2) and Porcine Reproductive and Respiratory Syndrome Virus (PRRSV) Potentiates PCV2 Replication"; Archives of Virology, 2000, pp. 2421-2429, vol. 145.
Allan, G. M. et al., "Isolation of Porcine Circovirus-like Viruses from Pigs with a Wasting Disease in the USA and Europe"; Journal of Veterinary Diagnostic Investigation, 1998, pp. 3-10, vol. 10.
Allan, G. M. et al., "PMWS: Experimental Model and Co-infections"; Veterinary Microbiology , 2004, vol. 98, pp. 165-168.
An, D. J. et al., "Phylogenetic Characterization of Porcine Circovirus Type 2 in PMWS and PDNS Korean pigs between 1999 and 2006"; Virus Research, 2007, pp. 115-122, vol. 129.
Bolin, S. R. et al., "Postweaning Multisystemic Wasting Syndrome Induced after Experimental Inoculation of Cesarean-Derived, Colostrum-deprived Piglets with Type 2 Porcine Circovirus"; Journal of Veterinary Diagnostic Investigation, 2001, pp. 185-194, vol. 13.
Carman, S. et al., "The Emergence of a New Strain of Porcine Circovirus-2 in Ontario and Quebec Swine and its Association with Severe Porcine Circovirus Associated Disease—2004-2006"; Canadian Journal of Veterinary Research, 2008, pp. 259-268, vol. 72.
Chae, J. S. and K. S. Choi, "Genetic Diversity of Porcine Circovirus Type 2 from Pigs in Republic of Korea"; Research in Veterinary Science, 2009, pp. 333-338, vol. 88.
Chae, J. S. and K. S. Choi, "Evidence of Shedding of Porcine Circovirus Type 2 in Milk from Experimentally Infected Sows"; 2009, Research in Veterinary Science, pp. 108-110, vol. 86.
Cheung, A. K., "Comparative Analysis of the Transcriptional Patterns of Pathogenic and Nonpathogenic Porcine Circoviruses"; Virology, 2003, pp. 41-49, vol. 310.
Cheung, A. K.Et al., "Detection of Two Porcine Circovirus Type 2 Genotypic Groups in United States Swine Herds"; Archives of Virology, 2007, pp. 1035-1044, vol. 152.
Ciacci-Zanella, J. R. et al., "Detection of Porcine Circovirus Type 2 (PCV2) Variants PCV2-1 and PCV2-2 in Brazilian Pig Population"; Research Veterinary Science, 2009, pp. 157-160, vol. 87.
Dupont, K. et al., "Genomic Analysis of PCV2 Isolates from Danish Archives and a Current PMWS Case-Control Study Supports a Shift in Genotypes with Time"; Veterinary Microbiology, 2008, pp. 56-64, vol. 128.
DuPont, K.et al., "Examination for a Viral Co-factor in Postweaning Multisystemic Wasting Syndrome (PMWS)", Veterinary Microbiology, 2008, pp. 97-107, vol. 129.
Ellis, J. et al., "Isolation of Circovirus from Lesions of Pigs with Postweaning Muitisystemic Wasting Syndrome"; Canadian Veterinary Journal, 1998, pp. 44-51, vol. 39.
Ellis, J. et al., "Porcine Circovirus-2 and Concurrent Infections in the Field"; Veterinary Microbiology, 2004, pp. 159-163, vol. 98.
Fenaux, M. et al., "Detection and in vitro and in vivo Characterization of Porcine Circovirus DNA from a Porcine-Derived Commercial Pepsin Product"; Journal of General Virology, 2004, pp. 3377-3382, vol. 85.
Finsterbusch, T. and A. Mankertz, "Porcine Circoviruses—Small but Powerful", Virus Research , 2009, pp. 177-183, vol. 143.

Fort, M. et al., "Porcine Circovirus Type 2 (PCV2) Vaccination of Conventional Pigs Prevents Viremia against PCV2 Isolates of Different Genotypes and Georgraphic Origins", Vaccine, 2008, pp. 1063-1071, vol. 26.
Fort, M. et al., "One Dose of a Porcine Circovirus 2 (PCV2) Sub-Unit Vaccine Administered to 3-week-old Conventional Piglets Elicits Cell-Mediated Immunity and Significantly Reduces PCV2 Viremia in an Experimental Model"; Vaccine, 2009, pp. 4031-4037, vol. 27.
Gagnon, C. A. et al., "The Emergence of Porcine Circovirus 2b Genotype (PCV-2b) in Swine in Canada"; Canadian Veterinary Journal, 2007, pp. 811-819, vol. 48.
Gillespie, J. et al, "Porcine Circovirus Type 2 and Porcine Circovirus-Associated Disease"; Journal of Veterinary Internal Medicine, 2009, pp. 1151-1163, vol. 23.
Gillespie, J. et al., "A Genetically Engineered Chimeric Vaccine against Porcine Circovirus Type 2 (PCV2) is Genetically Stable in vitro and in vivo"; Vaccine, 2008, pp. 4231-4236, vol. 26.
Mankertz, A. et al., "Molecular Biology of Porcine Circovirus: Analyses of Gene Expression and Viral Replication"; Veterinary Microbiology, 2004,:pp. 81-88, vol. 98.
Hamel, A. L. et al., "Nucleotide Sequence of Porcine Circovirus Associated with Postweaning Multisystemic Wasting Syndrome in Pigs"; Journal of Virology, 1998, pp. 5262-5267, vol. 72.
Harms, P. A. et al., "Experimental Reproduction of Severe Disease in CD/CD Pigs Concurrently Infected with Type 2 Porcine Circovirus and Porcine Reproductive and Respiratory Syndrome Virus"; Veterinary Pathology, 2001, pp. 528-539, vol. 38.
Kennedy, S. et al., Reproduction of Lesions of Postweaning Multisystemic Wasting Syndrome by Infection of Conventional Pigs with Porcine Circovirus Type 2 Alone or in Combination with Porcine Parvovirus; Journal of Comparative Pathology, 2000, pp. 9-24, vol. 122.
Lager, K. M et al., 2007, "Mortality in Pigs Given Porcine Circovirus Type 2 Subgroup 1 and 2 Viruses Derived from DNA Clones"; Veterinary Record, 2007, pp. 428-429, vol. 161.
Lekcharoensuk, P. et al., "Epitope Mapping of the Major Capsid Protein of Type 2 Porcine Circovirus (PCV2) by Using Chimeric PCV1 and PCV2"; Journal of Virology , 2004, pp. 8135-8145, vol. 78.
Lipej, Z. et al., "Postweaning Multisystemic Wasting Syndrome (PMWS) in Pigs in Croatia: Detection and Characterisation of Porcine Circovirus Type 2 (PCV2)"; Acta Veterinaria Hungarica, 2005, pp. 385-396, vol. 53.
Meehan, B. M. et al., "Characterization of Novel Circovirus DNAs Associated with Wasting Syndromes in Pigs"; Journal of General Virology, 1998, pp. 2171-2179, vol. 79.
Madson, D. M. et al., "Characterization of Shedding Patterns of Porcine Circovirus Types 2a and 2b in Experimentally Inoculated Mature Boars"; Journal of Veterinary Diagnostic Investigation , 2008, pp. 725-734, vol. 20.
Mankertz, A. and B. Hillenbrand, "Replication of Porcine Circovirus Type 1 Requires Two Proteins Encoded by the Viral Rep Gene"; Virology, 2001, pp. 429-438, vol. 279.
Nawagitgul, P. et al., "Open Reading Frame 2 of Porcine Circovirus Type 2 Encodes a Major Capsid Protein"; Journal of General Virology, 2000, pp. 2281-2287, vol. 81.
Olvera, A. et al., "Molecular Evolution of Porcine Circovirus Type 2 Genomes: Phylogeny and Clonality"; Virology, 2007, pp. 175-185, vol. 357.
Ramamoorthy, Sheela, et al., Supra; "Porcine Circoviruses: A Minuscule Yet Mammoth Paradox"; Animal Health Research Reviews, 2008, pp. 1-20, vol. 10.
Roca, M. et al., "In vitro and in vivo Characterization of an Infectious Clone of a European Strain of Porcine Circovirus Type 2"; 2004, Journal of General Virology, pp. 1259-1266, vol. 85.
Opriessnig, T. et al., "Genetic and Experimental Comparison of Porcine Circovirus Type 2 (PCV2) Isolates from Cases with and without PCV2-Associated Lesions Provides Evidence for Differences in Virulence"; Journal of General Virology , 2006, pp. 2923-2932, vol. 87.
Opriessnig, T. et al., Porcine Circovirus Type 2 Associated Disease: Update on Current Terminology, Clinical Manifestations, Pathogen-

(56) References Cited

OTHER PUBLICATIONS esis, Diagnosis, and Intervention Strategies; Journal of Veterinary Diagnostic Investigation, 2007, pp. 591-615, vol. 19.
Opriessnig, T. et al., Differences in Virulence among Porcine Circovirus Type 2 Isolates are Unrelated to Cluster Type 2a or 2b and Prior Infection Provides Heterologous Protection; Journal of General Virology, 2008, pp. 2482-2491, vol. 89.
Opriessnig, T. et al., "Comparison of Efficacy of Commercial One Dose and Two Dose PCV2 Vaccines using a Mixed PRRSV-PCV2-SIV Clinical Infection Model 2-3-Months Post Vaccination"; 2009, Vaccine, pp. 1002-1007, vol. 27.
Rovira, A. et al., "Experimental Inoculation of Conventional Pigs with Porcine Reproductive and Respiratory Syndrome Virus and Porcine Circovirus 2"; Journal of Virology , 2002, pp. 3232-3239, vol. 76.
Segales, J. et al., "Porcine Circovirus Diseases"; Animal Health Research Review, 2005, pp. 119-142, vol. 6.
Segales, J. et al., "PCV-2 Genotype Definition and Nomenclature"; Veterinary Record , 2008, pp. 867-868, vol. 162.
Shang, S. B. et al., "Fine Mapping of Antigenic Epitopes on Caspid Proteins of Porcine Circoviurs, and Antigenic Phenotype of Porcine Circovirus Type 2"; Molecular Immunology, 2009, pp. 327-334, vol. 46.
Tischer, I. et al., "Studies on Epidemiology and Pathogenicity of Porcine Circovirus"; Archives of Viroligy, 1986, pp. 271-276, vol. 91.
European Search Report dated Sep. 12, 2013.
Beach, Nathan M. et al; Novel Chimeric Porcine Circovirus (PCV) with the Capsid Gene of the Emerging PCV2b Subtype Cloned in the Genomic Backbone of the Non-Pathogenic PCV1 is Attentuated in vivo and Induces Protective and Cross-Protective Immunity Against PCV2b and PCVa Subtypes in Pigs; pp. 221-232; (2011); vol. 29, No. 2; Elsevier.
Beach, N.M. et al; Replacement of the Replication Factors of Porcine Circovirus (PCV) Type 2 with Those of PCV Type 1 Greatly Enhances Viral Replication In Vitro; pp. 8986-8989, (2010); vol. 84, No. 17; Journal of Virology.
Cheung, Andrew K. et al; Identification of an Amino Acid Domain Encoded by the Capsid Gene of Porcine Circovirus Type 2 the Modulates Intracellular Viral Protein Distribution During Replication; pp. 358-362; (2011); vol. 155, No. 1; Virus Research.
GenBank: EU340258.1.
Opriessnig, Tanja et al., A PCV2 Vaccine based on genotype 2b is more effective than a 2a-based vaccine to protect against PCV2b or combined PCV2a/2b viremia in pigs with concurrent PCV2, PRRSV and PPV infection, Elsevier; Vaccine, vol. 31, 2013, p. 487-494.
Nathan M. Beach et al.; "Novel chimeric porcine circovirus (PCV) with the capsid gene of the emerging PCV2b subtype cloned in the genomic backbone of the non-pathogenic PCV1 is attenuated in vivo and induces protective and cross-protective immunity against PCV2ba and PCV2a subtypes in pigs"; Vaccine; vol. 29; 2011; pp. 221-232.
Tanja Opriessnig et al.; "Porcine circovirus type 2-associated disease: Update on current terminology, clinical manifestations, pathogenesis, diagnosis, and intervention strategies"; J. Vet Diagn Invest; vol. 19; 2007; pp. 591-615.
M. Fort et al.; "Porcine circovirus type 2 (PCV2) vaccination of conventional pigs prevents viremia against PCV2 isolates of different genotypes and geographic origins"; Vaccine; vol. 26; 2008; pp. 1063-1071.

\* cited by examiner

SEQUENCE LISTING

<160> NUMBER OF SEQ ID NOS: 18

<210> SEQ ID NO 1
<211> LENGTH: 1768
<212> TYPE: DNA
<213> ORGANISM: Porcine circovirus

<400> SEQUENCE: 1

```
cttttttatc acttcgtaat ggttttatt attcatttag ggtttaagtg gggggtcttt      60
aagattaaat tctctgaatt gtacatacat ggttacacgg atattgtagt cctggtcgta     120
tatactgttt tcgaacgcag tgccgaggcc tacgtggtcc acatttctag aggtttgtag     180
cctcatccaa agctgattcc ttttgttatt tggttggaag taatcaatgg tggagtcaag     240
aacaggtttg ggtgtgaagt aacgggagtg gtaggagaag ggttggggga ttgtatggcg     300
ggaggagtag tttacatatg ggtcataggt tagggctgtg gcctttgtta caaagttatc     360
atctagaata acagcagtgg agcccactcc cctatcaccc tgggtgatgg gggagcaggg     420
ccagaattca accttaacct ttcttattct gtagtattca aagggtatag agattttgtt     480
ggtcccccct cccgggggaa caaagtcgtc aatattaaat ctcatcatgt ccaccgccca     540
ggagggcgtt ctgactgtgg tagccttgac agtatatccg aaggtgcggg agaggcgggt     600
gttgaagatg ccattttttcc ttctccaacg gtagcggtgg cggggtgga cgagccaggg     660
gcggcggcgg aggatctggc caagatggct gcggggcgg tgtcttcttc tgcggtaacg     720
cctccttgga tacgtcatag ctgaaaacga aagaagtgcg ctgtaagtat taccagcgca     780
cttcggcagc ggcagcacct cggcagcacc tcagcagcaa catgcccagc aagaagaatg     840
gaagaagcgg accccaacca cataaaaggt gggtgttcac gctgaataat ccttccgaag     900
acgagcgcaa gaaaatacgg gagctcccaa tctccctatt tgattatttt attgttggcg     960
aggagggtaa tgaggaagga cgaacacctc acctccaggg gttcgctaat tttgtgaaga    1020
agcaaacttt taataaagtg aagtggtatt tgggtgcccg ctgccatatc gagaaagcca    1080
aaggaactga tcagcagaat aaagaatatt gcagtaaaga aggcaactta cttattgaat    1140
gtggagctcc tcgatctcaa ggacaacgga gtgacctgtc tactgctgtg agtaccttgt    1200
tggagagcgg gagtctggtg accgttgcag agcagcaccc tgtaacgttt gtcagaaatt    1260
tccgcgggct ggctgaactt tgaaagtga gcgggaaaat gcagaagcgt gattggaaga    1320
ccaatgtaca cgtcattgtg gggccacctg ggtgtggtaa aagcaaatgg ctgctaattt    1380
ttgcagaccc ggaaaccaca tactggaaac cacctagaaa caagtggtgg atggttacc     1440
atggtgaaga agtggttgtt attgatgact tttatggctg gctgccgtgg gatgatctac    1500
tgagactgtg tgatcgatat ccattgactg tagagactaa aggtggaact gtacctttt     1560
tggcccgcag tattctgatt accagcaatc agacccgtt ggaatggtac tcctcaactg    1620
ctgtcccagc tgtagaagct ctctatcgga ggattacttt cttggtattt tggaagaatg    1680
ctacagaaca atccacggag gaaggggcc agttcgtcac cctttccccc ccatgccctg    1740
aatttccata tgaaataaat tactgagt                                       1768
```

<210> SEQ ID NO 2
<211> LENGTH: 1767
<212> TYPE: DNA
<213> ORGANISM: Porcine circovirus

<400> SEQUENCE: 2

```
cttttttatc acttcgtaat ggttttatt attcattaag ggttaagtgg gggtctttta      60
```

```
agattaaatt ctctgaattg tacatacatg gttacacgga tattgtattc ctggtcgtat      120
atactgtttt cgaacgcagt gccgaggcct acgtggtcta catttccagc agtttgtagt      180
ctcagccaca gctggtttct tttgttgttt ggttggaagt aatcaatagt ggaatctagg      240
acaggtttgg gggtaaagta gcgggagtgg taggagaagg gctgggttat ggtatggcgg      300
gaggagtagt ttacataggg gtcataggtg agggctgtgg cctttgttac aaagttatca      360
tctagaataa cagcactgga gcccactccc ctgtcaccct gggtgatcgg ggagcagggc      420
cagaattcaa ccttaacctt tcttattctg tagtattcaa agggcacaga gcggggtttt      480 gagcccctc ctgggggaag aaagtcatta atattgaatc tcatcatgtc caccgcccag      540
gagggcgttc tgactgtggt tcgcttgata gtatatccga aggtgcggga taggcgggtg      600
ttgaagatgc catttttcct tctccagcgg taacggtggc gggggtggac gagccagggg      660
cggcggcgga ggatctggcc aagatggctg cgggggcggt gtcttcttct ccggtaacgc      720
ctccttggat acgtcatagc tgaaaacgaa agaagtgcgc tgtaagtatt accagcgcac      780
ttcggcagcg gcagcacctc ggcagcacct cagcagcaac atgcccagca agaagaatgg      840
aagaagcgga ccccaacccc ataaaaggtg ggtgttcact ctgaataatc cttccgaaga      900
cgagcgcaag aaaatacggg atcttccaat atccctattt gattatttta ttgttggcga      960
ggagggtaat gaggaaggac gaacacctca cctccagggg ttcgctaatt tgtgaagaa     1020 gcagactttt aataaagtga agtggtattt gggtgcccgc tgccacatcg agaaagccaa     1080
aggaacagat cagcagaata agaatactg cagtaaagaa ggcaacttac tgattgagtg     1140
tggagctcct agatctcagg gacaacggag tgacctgtct actgctgtga gtaccttgtt     1200
ggagagcggg agtctggtga ccgttgcaga gcagtaccct gtaacgtttg tcagaaattt     1260
ccgcgggctg gctgaacttt tgaaagtgag cgggaaaatg cagaagcgtg attggaagac     1320
taatgtacac gtcattgtgg ggccacctgg gtgtggtaaa agcaaatggg ctgctaattt     1380
tgcagacccg gaaaccacat actggaaacc acctagaaac aagtggtggg atggttacca     1440
tggtgaagaa gtggttgtta ttgatgactt ttatggctgg ctgccctggg atgatctact     1500
gagactgtgt gatcgatatc cattgactgt agagactaaa ggtggaactg taccttttt     1560 ggcccgcagt attctgatta ccagcaatca gaccccgttg gaatggtact cctcaactgc     1620
tgtcccagct gtagaagctc tttatcggag gattacttcc ttggtatttt ggaagaatgc     1680
tacagaacaa tccacggagg aagggggcca gttcgtcacc ctttcccccc catgccctga     1740
atttccatat gaaataaatt actgagt                                         1767
```

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 3

```
tttccgcggg ctggctgaac ttttgaaag                                        29
```

<210> SEQ ID NO 4
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 4
agcccgcgga aatttctgac aaacgttac                              29

<210> SEQ ID NO 5
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 5
cgtaatggtt tttatttta agggttaagt gg                           32

<210> SEQ ID NO 6
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 6
ctttcacttt tataggatga cgtatccaag gagg                        34

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
ttcgggtacc cgaaggccga tt                                     22

<210> SEQ ID NO 8
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 8
cacttaaccc ttaaaaataa aaaccattac gat                         33

<210> SEQ ID NO 9
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 9
cctccttgga tacgtcatcc tataaaagtg aaag                        34

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
cagtggatcc cccgggctgc agga                                   24

<210> SEQ ID NO 11
<211> LENGTH: 22

```
<212> TYPE: DNA
<213> ORGANISM: Artificial Sequence
<220> FEATURE:
<223> OTHER INFORMATION: Synthetic oligonucleotide

<400> SEQUENCE: 11
ataacccagc ccttctccta cc                                                  22

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
ggcctacgtg gtctacattt cc                                                  22

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
aaaagcaaat gggctgctaa                                                     20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tggtaaccat cccaccactt                                                     20

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
tgttgaagat gccatttttc c                                                   21

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
gaggagttct accctcttcc                                                     20

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
```

-continued

```
tgttgaagat gccatttttc c                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
gaggtgttcg tccttcctca                                                20
```

LIVE ATTENUATED CHIMERIC PORCINE CIRCOVIRUS VACCINE

REFERENCE TO RELATED APPLICATION

This patent application claims the benefit of U.S. Provisional Patent Application No. 61/314,362, filed on Mar. 16, 2010, whose disclosures are hereby incorporated by reference in their entirety into the present disclosure.

FIELD OF INVENTION

The present invention relates to infectious DNA clone, live attenuated and inactivated vaccines of porcine circovirus (PCV), particularly chimeric virus of PCV1 and PCV2, particularly subtype PCV2b, and methods for protecting against PCV infection and porcine circovirus-associated disease (PCVAD).

BACKGROUND OF THE INVENTION

Porcine circovirus (PCV) is a small, non-enveloped DNA virus which belongs to the family Circoviridae (Todd, D. et al., 2005, Circoviridae, p. 327-334. In C. M. Fauquet et al (ed.), Virus Taxonomy: Eighth Report of the International Committee on Taxonomy of Viruses, Elsevier Academic Press, San Diego). Type 1 PCV (PCV1) was discovered as a contaminant of the porcine kidney PK-15 cell line in the mid-seventies (Tischer, I. et al., 1974, Characterization of papovavirus- and picornavirus-like particles in permanent pig kidney cell lines, Zentralbl Bakteriol Orig A 226:153-67).

PCV1 was considered to be a non-pathogenic virus because inoculation of pigs with the PK-15 cell line-derived PCV1 virus did not cause any disease in pigs (Tischer, I. et al., 1986, Studies on epidemiology and pathogenicity of porcine circovirus, Arch Virol 91:271-6). In 1997, a variant strain of PCV, designated PCV type-2 (PCV2), was discovered in piglets with wasting disease in Canada (Allan, G. M. et al., 1998, Isolation of porcine circovirus-like viruses from pigs with a wasting disease in the USA and Europe. J Vet Diagn Invest 10:3-10; Clark, E. G., 1997, Presented at the 28th Annual Meeting of the American Association of Swine Practitioners; Ellis, J. et al., 1998, Isolation of circovirus from lesions of pigs with postweaning muitisystemic wasting syndrome, Can Vet J 39:44-51; Meehan, B. M. et al., 1998, Characterization of novel circovirus DNAs associated with wasting syndromes in pigs, J Gen Virol 79 (Pt 9):2171-9). Currently, PCV2 is the primary causative agent of porcine circovirus-associated disease (PCVAD), which includes wasting, mortality, respiratory signs, enteritis, reproductive failure, and porcine dermatitis and nephropathy syndrome (PDNS) (Opriessnig, T. et al., 2007, Porcine circovirus type 2 associated disease: update on current terminology, clinical manifestations, pathogenesis, diagnosis, and intervention strategies, J Vet Diagn Invest 19:591-615). PCV2 is currently considered to be one of the most economically-important viral pathogens in global pig populations, and is found in every major swine producing country of the world (Gillespie, J. et al, 2009, Porcine Circovirus Type 2 and Porcine Circovirus-Associated Disease, J Vet Intern Med). Observation of severe clinical PCVAD in conventional pigs experimentally infected with PCV2 alone is uncommon, and coinfection with other swine pathogens such as porcine reproductive and respiratory syndrome virus (PRRSV) or porcine parvovirus (PPV) is usually required to induce the full-spectrum of clinical PCVAD (Allan, G. M. et al., 2000, Experimental infection of colostrum deprived piglets with porcine circovirus 2 (PCV2) and porcine reproductive and respiratory syndrome virus (PRRSV) potentiates PCV2 replication, Arch Virol 145:2421-9; Opriessnig, T. et al. 2007. Supra; Roca, M. et al., 2004, In vitro and in vivo characterization of an infectious clone of a European strain of porcine circovirus type 2, J Gen Virol 85:1259-66; Rovira, A. et al., 2002, Experimental inoculation of conventional pigs with porcine reproductive and respiratory syndrome virus and porcine circovirus 2, J Virol 76:3232-9; Tomas, A. et al., 2008, A meta-analysis on experimental infections with porcine circovirus type 2 (PCV2), Vet Microbiol 132:260-73). However, infection of caesarean-derived, colostrum-deprived (CD/CD) pigs with PCV2 alone has resulted in severe clinical PCVAD and mortality (Allan, G. et al. 2003, Reproduction of postweaning muitisystemic wasting syndrome in pigs experimentally inoculated with a Swedish porcine circovirus 2 isolate, J Vet Diagn Invest 15:553-60; Allan, G. M. et al., 2004, PMWS: experimental model and co-infections, Vet Microbiol 98:165-8; Bolin, S. R. et al., 2001, Postweaning multisystemic wasting syndrome induced after experimental inoculation of cesarean-derived, colostrum-deprived piglets with type 2 porcine circovirus, J Vet Diagn Invest 13:185-94; Harms, P. A. et al., 2001, Experimental reproduction of severe disease in CD/CD pigs concurrently infected with type 2 porcine circovirus and porcine reproductive and respiratory syndrome virus, Vet Pathol 38:528-39; Kennedy, S. et al., 2000, Reproduction of lesions of postweaning muitisystemic wasting syndrome by infection of conventional pigs with porcine circovirus type 2 alone or in combination with porcine parvovirus, J Comp Pathol 122:9-24). Several comprehensive reviews of the pathogenesis, immunology, and molecular biology of PCV2 are available (Allan, G. M. and J. A. Ellis, 2000, Porcine circoviruses: a review. J Vet Diagn Invest 12:3-14; Ellis, J. et al., 2004, Porcine circovirus-2 and concurrent infections in the field, Vet Microbiol 98:159-63; Finsterbusch, T. and A. Mankertz, 2009, Porcine circoviruses-small but powerful, Virus Res 143:177-83; Gillespie, J. et al., 2009, supra; Mankertz, A. et al., 2004, Molecular biology of Porcine circovirus: analyses of gene expression and viral replication, Vet Microbiol 98:81-8; Opriessnig, T. et al. 2007, Supra; Ramamoorthy, S. and X. J. Meng, 2009, Porcine circoviruses: a minuscule yet mammoth paradox, Anim Health Res Rev 10:1-20; Segales, J. et al., 2005, Porcine circovirus diseases, Anim Health Res Rev 6:119-42).

Although the genomic organization of the pathogenic PCV2 and the non-pathogenic PCV1 is similar, the genomes of PCV1 and PCV2 share only approximately 68-76% nucleotide sequence identity (Fenaux, M. et al., 2004, Detection and in vitro and in vivo characterization of porcine circovirus DNA from a porcine-derived commercial pepsin product, J Gen Virol 85:3377-82; Hamel, A. L et al., 1998, Nucleotide sequence of porcine circovirus associated with postweaning muitisystemic wasting syndrome in pigs, J Virol 72:5262-7; Tischer, I. et al., 1982, A very small porcine virus with circular single-stranded DNA, Nature 295:64-6) and differences in transcriptional patterns and antigenic profile of the capsid protein have been reported (Cheung, A. K. 2003, Comparative analysis of the transcriptional patterns of pathogenic and nonpathogenic porcine circoviruses, Virology 310:41-9; Lekcharoensuk, P. et al., 2004, Epitope mapping of the major capsid protein of type 2 porcine circovirus (PCV2) by using chimeric PCV1 and PCV2, J Virol 78:8135-45; Shang, S. B. et al., 2009, Fine mapping of antigenic epitopes on capsid proteins of porcine circovirus, and antigenic phenotype of porcine circovirus type 2, Mol Immunol 46:327-34). The two major genes encoded by the viral genome include the 942 bp replicase (rep) gene (Mankertz, A. and B. Hillenbrand, 2001, Replication of porcine circovirus type 1 requires two proteins encoded by the viral rep gene, Virology 279:429-38) and the 702 bp capsid gene (cap) (Nawagitgul, P. et al., 2000, Open reading frame 2 of porcine circovirus type 2 encodes a major capsid protein, J Gen Virol 81:2281-7). The rep gene is highly conserved between PCV1 and PCV2 with about 83% nucleotide sequence identity while the cap gene shares only about 67-70% identity (Mankertz, A. et al., 2004, supra). Currently, at least three subtypes of PCV2 have been identified in swine herds worldwide: PCV2a, PCV2b, and PCV2c (Dupont, K. et al., 2008, Genomic analysis of PCV2 isolates from Danish archives and a current PMWS case-control study supports a shift in genotypes with time, Vet Microbiol 128:56-64; Segales, J. et al., 2008, PCV-2 genotype definition and nomenclature, Vet Rec 162:867-8). PCV2a and PCV2b have both been associated with clinical PCVAD of varying degrees of severity (An, D. J. et al., 2007, Phylogenetic characterization of porcine circovirus type 2 in PMWS and PDNS Korean pigs between 1999 and 2006, Virus Res 129:115-22; Ciacci-Zanella, J. R. et al., 2009, Detection of porcine Circovirus type 2 (PCV2) variants PCV2-1 and PCV2-2 in Brazilian pig population, Res Vet Sci 87:157-60; Lager, K. M et al., 2007, Mortality in pigs given porcine circovirus type 2 subgroup 1 and 2 viruses derived from DNA clones, Vet Rec 161:428-9; Madson, D. M. et al., 2008, Characterization of shedding patterns of Porcine circovirus types 2a and 2b in experimentally inoculated mature boars, J Vet Diagn invest 20:725-34; Opriessnig, T. et al., 2006, Genetic and experimental comparison of porcine circovirus type 2 (PCV2) isolates from cases with and without PCV2-associated lesions provides evidence for differences in virulence, J Gen Virol 87:2923-32; Opriessnig, T. et al., 2008, Differences in virulence among porcine circovirus type 2 isolates are unrelated to cluster type 2a or 2b and prior infection provides heterologous protection, J Gen Virol 89:2482-91). Prior to 2005, only PCV2a was found within pig populations in the United States and Canada, while both PCV2a and PCV2b were present in Europe and China (Chae, J. S. and K. S. Choi, 2009, Genetic diversity of porcine circovirus type 2 from pigs in Republic of Korea, Res Vet Sci; Dupont, K. et al., 2008, supra). Since 2005, novel PCV2b strains were recognized in the United States and there has been a global shift in a dominant prevalence of PCV2b in pig populations, concurrently with increased severity of clinical PCVAD (Carman, S. et al., 2008, The emergence of a new strain of porcine circovirus-2 in Ontario and Quebec swine and its association with severe porcine circovirus associated disease-2004-2006, Can J Vet Res 72:259-68; Chae, J. S. and K. S. Choi, 2009, supra; Cheung, A. K. et al., 2007, Detection of two porcine circovirus type 2 genotypic groups in United States swine herds, Arch Virol 152:1035-44; Ciacci-Zanella, J. R. et al., 2009, supra; Dupont, K. et al., 2008, supra; Gagnon, C. A. et al., 2007, The emergence of porcine circovirus 2b genotype (PCV-2b) in swine in Canada, Can Vet J 48:811-9; Lipej, Z. et al., 2005, Postweaning muitisystemic wasting syndrome (PMWS) in pigs in Croatia: detection and characterisation of porcine circovirus type 2 (PCV2), Acta Vet Hung 53:385-96; Wang, F. et al., 2009, Genetic variation analysis of Chinese strains of porcine circovirus type 2, Virus Res 145:151-6; Wiederkehr, D. D. et al., 2009, A new emerging genotype subgroup within PCV-2b dominates the PMWS epizooty in Switzerland, Vet Microbiol 136:27-35). The pathogenicity of PCV2c is unclear, as it has only been reported in non-diseased herds in Denmark in 1980, 1987, and 1990 (Dupont, K. et al., 2008, supra).

The current available commercial vaccines are all killed or recombinant vaccines based upon the PCV2a subtype (Opriessnig, T. et al. 2007, Supra; Ramamoorthy, S. and X. J. Meng, 2009, supra). The inventors have previously successfully developed an inactivated vaccine, Suvaxyn PCV2® One Dose™, based upon the PCV1-2a chimeric virus (with the capsid gene of PCV2a in the backbone of PCV1) (Fenaux, M. et al., 2004A, A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs, J Virol 78:6297-303; Fenaux, M. et al., 2003, Immunogenicity and pathogenicity of chimeric infectious DNA clones of pathogenic porcine circovirus type 2 (PCV2) and nonpathogenic PCV1 in weanling pigs, J Virol 77:11232-43; Gillespie, J. et al., 2008, A genetically engineered chimeric vaccine against porcine circovirus type 2 (PCV2) is genetically stable in vitro and in vivo, Vaccine 26:4231-6). However, since the PCV2b subtype has now become the globally dominant genotype associated with severe clinical PCVAD in commercial pigs, and since PCV2a and PCV2b differ by as much as 10% nucleotide sequence identity (Fenaux, M. et al., 2000, Genetic characterization of type 2 porcine circovirus (PCV-2) from pigs with postweaning muitisystemic wasting syndrome in different geographic regions of North America and development of a differential PCR-restriction fragment length polymorphism assay to detect and differentiate between infections with PCV-1 and PCV-2, J Clin Microbiol 38:2494-503; Olvera, A. et al., 2007, Molecular evolution of porcine circovirus type 2 genomes: phylogeny and clonality, Virology 357:175-85), it is unknown whether the current PCV2a subtype-based killed or recombinant vaccines provide complete protection against the newly-recognized PCV2b subtype. Several studies have demonstrated effectiveness of current commercial vaccines against PCV2b challenge (Fort, M. et al., 2008, Porcine circovirus type 2 (PCV2) vaccination of conventional pigs prevents viremia against PCV2 isolates of different genotypes and geographic origins, Vaccine 26:1063-71; Fort, M. et al., 2009, One dose of a porcine circovirus 2 (PCV2) sub-unit vaccine administered to 3-week-old conventional piglets elicits cell-mediated immunity and significantly reduces PCV2 viremia in an experimental model, Vaccine 27:4031-7; Opriessnig, T. et al., 2009, Comparison of efficacy of commercial one dose and two dose PCV2 vaccines using a mixed PRRSV-PCV2-SW clinical infection model 2-3-months post vaccination, Vaccine 27:1002-7), however it is imperative to develop a PCV2b subtype-based vaccine, preferably a live-attenuated vaccine, against PCVAD. A live-attenuated vaccine based on the new PCV2b subtype would possibly provide much greater protection in the field than the current available killed and subunit vaccines based on the PCV2a subtype.

SUMMARY OF THE INVENTION

The present invention provides a nucleic acid molecule of porcine circovirus (PCV) comprising a nucleic acid molecule encoding a nonpathogenic chimeric PCV derived from a genomic sequence of Type 1 PCV (PCV1), and at least a portion of an encoding sequence of a capsid protein of Type 2 PCV (PCV2), preferably of subtype PCV2b.

In one embodiment of the present invention, the encoding sequence of a capsid protein of PCV2 is selected from the group consisting subtypes PCV2a, PCV2b, and PCV2c.

In another embodiment of the present invention, the encoding sequence of a capsid protein of PCV2 is of subtype PCV2b.

In a further embodiment of the present invention, the encoding sequence of a capsid protein of PCV2 is at least a portion of open reading frame 2 (ORF2) of PCV2, preferably of subtype PCV2b.

In yet another embodiment of the present invention, the nucleic acid molecule encoding more than one copy of a nonpathogenic chimeric PCV derived from a genomic sequence of Type 1 PCV (PCV1), and at least a portion of an encoding sequence of a capsid protein of Type 2 PCV (PCV2), preferably of subtype PCV2b.

The present invention also provides a biologically functional plasmid or viral vector containing a nucleic acid molecule encoding a nonpathogenic chimeric PCV derived from a genomic sequence of Type 1 PCV (PCV1), and at least a portion of an encoding sequence of a capsid protein of Type 2 PCV (PCV2), preferably of subtype PCV2b.

The present invention further provides a suitable host cell transfected by a vector comprising a nucleic acid molecule encoding a nonpathogenic chimeric PCV derived from a genomic sequence of Type 1 PCV (PCV1), and at least a portion of an encoding sequence of a capsid protein of Type 2 PCV (PCV2), preferably of subtype PCV2b.

The present invention further provides an avirulent, infectious chimeric PCV produced by a suitable host cell transfected by a vector comprising a nucleic acid molecule encoding a nonpathogenic chimeric PCV derived from a genomic sequence of Type 1 PCV (PCV1), and at least a portion of an encoding sequence of a capsid protein of Type 2 PCV (PCV2), preferably of subtype PCV2b.

The present invention further provides an inactivated chimeric PCV comprising at least a portion of a capsid protein of Type 2 PCV (PCV2), preferably of subtype PCV2b.

In one embodiment of the present invention, the encoding sequence of a capsid protein of PCV2 is selected from the group consisting subtypes PCV2a, PCV2b, and PCV2c.

In another embodiment of the present invention, the encoding sequence of a capsid protein of PCV2 is of subtype PCV2b.

In a further embodiment of the present invention, the encoding sequence of a capsid protein of PCV2 is at least a portion of open reading frame 2 (ORF2) of PCV2.

The present invention further provides a viral vaccine comprising a physiologically acceptable carrier and an immunogenic amount of a member selected from the group consisting of: (a) a nucleic acid molecule of Porcine Circovirus (PCV) comprising a nucleic acid molecule encoding a chimeric, nonpathogenic PCV derived from a genomic sequence of Type 1 PCV (PCV1), and at least a portion of an encoding sequence of a capsid protein of Type 2 PCV (PCV2), (b) a biologically functional plasmid or viral vector containing a nucleic acid molecule of PCV comprising a nucleic acid molecule encoding a chimeric, nonpathogenic PCV derived from a genomic sequence of PCV1, and at least a portion of an encoding sequence of a capsid protein of PCV2, (c) an avirulent, infectious nonpathogenic chimeric PCV which contains a nucleic acid molecule of PCV comprising a nucleic acid molecule encoding a chimeric, nonpathogenic PCV derived from a genomic sequence of PCV1, and at least a portion of an encoding sequence of a capsid protein of PCV2, and (d) an inactivated chimeric PCV comprising at least a portion of a capsid protein of PCV2, preferably of PCV2b subtype.

In one embodiment of the present invention, the vaccine contains live chimeric PCV virus.

In one embodiment of the present invention, the vaccine contains inactivated chimeric PCV virus.

In another embodiment of the present invention, the vaccine further contains an adjuvant.

In a further embodiment of the present invention, the vaccine protects against PCV2a and PCV2b infection.

The present invention also provides a method of immunizing a pig against PCV2 viral infection, comprising administering to a pig an immunologically effective amount of a viral vaccine comprising a physiologically acceptable carrier and an immunogenic amount of a member selected from the group consisting of: (a) a nucleic acid molecule of Porcine Circovirus (PCV) comprising a nucleic acid molecule encoding a chimeric, nonpathogenic PCV derived from a genomic sequence of Type 1 PCV (PCV1), and at least a portion of an encoding sequence of a capsid protein of Type 2 PCV (PCV2), (b) a biologically functional plasmid or viral vector containing a nucleic acid molecule of PCV comprising a nucleic acid molecule encoding a chimeric, nonpathogenic PCV derived from a genomic sequence of PCV1, and at least a portion of an encoding sequence of a capsid protein of PCV2, (c) an avirulent, infectious nonpathogenic chimeric PCV which contains a nucleic acid molecule of PCV comprising a nucleic acid molecule encoding a chimeric, nonpathogenic PCV derived from a genomic sequence of PCV1, and at least a portion of an encoding sequence of a capsid protein of PCV2, and (d) an inactivated chimeric PCV comprising at least a portion of a capsid protein of PCV2, preferably of PCV2b subtype.

In one embodiment of the present invention, the method comprising administering the nucleic acid molecule or live attenuated chimeric PCV virus to the pig.

In one embodiment of the present invention, the method comprising administering the inactivated chimeric PCV virus to the pig.

In another embodiment of the present invention, the method comprising administering the vaccine parenterally, intranasally, intradermally, or transdermally to the pig.

In a further embodiment of the present invention, the method comprising administering the vaccine intralymphoidly or intramuscularly to the pig.

The present invention also provides a method of protecting a pig against porcine circovirus-associated disease (PCVAD), comprising administering to a pig an immunologically effective amount of a viral vaccine comprising a physiologically acceptable carrier and an immunogenic amount of a member selected from the group consisting of: (a) a nucleic acid molecule of Porcine Circovirus (PCV) comprising a nucleic acid molecule encoding a chimeric, nonpathogenic PCV derived from a genomic sequence of Type 1 PCV (PCV1), and at least a portion of an encoding sequence of a capsid protein of Type 2 PCV (PCV2), (b) a biologically functional plasmid or viral vector containing a nucleic acid molecule of PCV comprising a nucleic acid molecule encoding a chimeric, nonpathogenic PCV derived from a genomic sequence of PCV1, and at least a portion of an encoding sequence of a capsid protein of PCV2, (c) an avirulent, infectious nonpathogenic chimeric PCV which contains a nucleic acid molecule of PCV comprising a nucleic acid molecule encoding a chimeric, nonpathogenic PCV derived from a genomic sequence of PCV1, and at least a portion of an encoding sequence of a capsid protein of PCV2, and (d) an inactivated chimeric PCV comprising at least a portion of a capsid protein of PCV2, preferably of subtype PCV2b.

BRIEF DESCRIPTION OF THE DRAWINGS

The above-mentioned features of the invention will become more clearly understood from the following detailed description of the invention read together with the drawings in which:

FIG. 1 illustrates the construction and genomic organization of full-length PCV2b and chimeric PCV1-2b DNA clones. FIG. 1(A) shows a PCV2b monomeric DNA clone. Complete genome of wildtype PCV2b was cloned in pBSK+ vector using unique Sac II site after amplification with PCR primers A (SEQ ID No:3) and B (SEQ ID No:4)(Table 1). FIG. 1(B) shows Chimeric PCV1-2b monomeric DNA clone. Chimeric PCV1-2b DNA clone was constructed by overlap extension PCR using PCR primers C-H (SEQ ID No:5-10)(Table 1).

FIG. 2 illustrates PCV2 capsid-specific antibody response in caesarean-derived colostrum-deprived (CD/CD) pigs experimentally inoculated with the chimeric PCV1-2b virus and the wildtype PCV2b virus. The mean serum S/P ratio+/−SEM is plotted for each treatment group throughout the experiment, with (*) indicating significant differences on that day. Due to death or early euthanasia of some PCV2b-infected pigs, fewer than five pigs were sampled in that group at 35-42 dpi. Groups with different letters are significantly different on that day.

FIG. 3 shows comparison of the overall lymphoid lesion scores at 21 dpi in the caesarean-derived colostrum-deprived (CD/CD) pigs inoculated with PBS buffer, chimeric PCV1-2b virus, and wildtype PCV2b virus. Combined lymphoid depletion, histiocytic replacement, and PCV2-specific antigen scores for the lymph nodes, spleen, and tonsil were compared between treatments. The PCV2b-inoculated pig that died at 18 dpi was included in the analysis. Circles indicate median, boxes are $1^{st}$ and $3^{rd}$ quartiles, and whiskers indicate total range of data. Treatments with different letters are significantly different.

FIG. 4 illustrates the quantification of viral DNA loads in serum and lymphoid tissues in caesarean-derived colostrum-deprived (CD/CD) pigs experimentally inoculated with the chimeric PCV1-2b virus and PCV2b virus. FIG. 4(A) shows a quantification of viremia and viral DNA loads in sera using qPCR. Group mean log viral genomic copies/ml of serum+/−SEM is plotted for each treatment group, with (*) indicating significant differences on that day. All samples at 0 dpi as well as all samples from PBS-inoculated pigs were negative. Due to death or early euthanasia of some PCV2b-infected pigs, fewer than five pigs were sampled in that group at 35-42 dpi. FIG. 4(B) shows a quantification of viral DNA load in TBLN tissues using qPCR. Lymph node tissue viral DNA loads determined for each pig are plotted on the day they died or were euthanized, with group means+/−SEM plotted at 21 and 42 dpi. All samples from PBS-inoculated pigs were negative, and PCV2b-infected pigs that died or were euthanized early due to PCVAD (filled circles) were not included in the analysis of group means. The (*) indicates significant differences on that day.

FIG. 5 illustrates PCV2-specific antibody response in conventional specific-pathogen-free pigs vaccinated with the chimeric PCV1-2b virus and subsequently challenged with PCV2a or PCV2b wildtype virus. The mean serum S/P ratio+/−SEM is plotted for each treatment group throughout the experiment, with (*) indicating significant differences between vaccinated (vax) and unvaccinated (PBS) groups. All pigs were challenged with PCV2a or PCV2b at 56 dpv. Groups with different letters at 77 dpv (or 21 dpc) are significantly different on that day.

FIG. 6 shows a comparison of overall lymphoid lesion scores in conventional SPF pigs vaccinated with PCV1-2b or PBS buffer and subsequently challenged with PCV2a or PCV2b. Combined lymphoid depletion, histiocytic replacement, and PCV2-specific antigen scores for the lymph nodes, spleen, and tonsil were compared between vaccinated and unvaccinated pigs by challenge PCV2 virus subtype. Circles indicate median, boxes are $1^{st}$ and $3^{rd}$ quartiles, and whiskers indicate the range of data. Pairs of treatments with (*) are significantly different.

FIG. 7 illustrates detection and quantification of PCV2 viral DNA loads in serum and lymphoid tissue samples in conventional pigs vaccinated with PBS buffer or PCV1-2b and subsequently challenged with PCV2a or PCV2b. FIG. 7(A) shows a quantification of viremia and viral loads in sera using qPCR. Group mean log viral genomic copies/ml of serum+/−SEM is plotted for each treatment group. All samples at 56 dpv (or 0 dpc) as well as all samples from vaccinated pigs were negative for PCV2a or PCV2b DNA. FIG. 7(B) shows a quantification of viral DNA loads in TBLN tissues using qPCR. Median viral DNA loads in lymphoid tissues determined for each pig are plotted. Circles indicate median, boxes are $1^{st}$ and $3^{rd}$ quartiles, and whiskers indicate the total range of data. Upon challenge with PCV2a or PCV2b, viral DNA was detected in the lymph nodes of all unvaccinated pigs, while only 1/10 vax/PCV2b pigs and 5/10 vax/PCV2a pigs had detectable viral DNA. The (*) indicates significant differences between vaccinated and unvaccinated pairs, based on challenge virus subtype.

DETAILED DESCRIPTION OF THE INVENTION

PCV2 infection and PCVAD continue to pose a major threat to global swine populations. PCVAD arguably is the most economically-important disease facing the swine industry today. Wasting, microscopic lesions of lymphoid depletion with histiocytic infiltration, and the presence of PCV2 antigen or DNA in the lesions are three characteristic criteria to diagnose PCVAD in a pig (Segales, J. et al., 2005, supra). It is known, however, that not all pigs infected with PCV2 will develop clinical PCVAD and coinfecting viral and bacterial pathogens are usually necessary to induce the full-spectrum of clinical PCVAD (Albina, E. et al., 2001, An experimental model for post-weaning muitisystemic wasting syndrome (PMWS) in growing piglets, J Comp Pathol 125:292-303; Magar, R. et al., 2000, Experimental transmission of porcine circovirus type 2 (PCV2) in weaned pigs: a sequential study, J Comp Pathol 123:258-69). Prior to 2005, the virus detected from PCVAD cases in the United States and Canada was almost exclusively of the PCV2a subtype. Consequently, four commercial vaccines all based on the PCV2a subtype were developed and are currently used worldwide in swine herds. The PCV2a strains isolated worldwide are closely-related and share 95 to 99% nucleotide sequence identities, and thus these commercial vaccines have been effective against PCV2a and PCVAD in the global swine populations.

Recently, the outbreaks of more severe PCVAD cases in certain areas in the United States and Canada have been attributed to the emergence of a new PCV2b subtype (Gagnon, C. A. et al., 2007, supra). The nucleotide sequences between PCV2a and PCV2b subtypes differ by as much as 10% and distinct amino acid sequence motifs distinguishing the two subtypes have been identified (Cheung, A. K. et al., 2007, supra), thus raising the question whether or not the current commercial vaccines based exclusively on PCV2a subtype can fully protect against the new PCV2b subtype infection. In the past few years, the PCV2 prevalence in the global swine herds has shifted to predominantly PCV2b subtype, and in fact, the majority of recent PCVAD cases in the United States are associated with the new PCV2b subtype (Cheung, A. K. et al., 2007, supra; Firth, C et al., 2009, Insights into the evolutionary history of an emerging livestock pathogen: porcine circovirus 2, J Virol 83:12813-21). The PCV2a subtype-based vaccines are still in use worldwide since the PCV2a vaccines have been shown to provide cross-protection (Fort, M. et al., 2008, supra; Fort, M. et al. 2009, supra; Opriessnig, T. et al., 2009, supra; Segales, J. et al., 2008, supra). However, the extent of cross-protection offered by the PCV2a-based vaccines against the circulating new PCV2b subtype is unknown, and the global swine industry will certainly be benefited from having access to a vaccine that is based on the currently-circulating predominant PCV2b subtype. Therefore, one of the objectives of the present invention is to develop a new generation vaccine based on the new PCV2b subtype, and to evaluate the efficacy of the PCV2b-based vaccine against both PCV2a and PCV2b challenges.

The present invention provides an attenuated live chimeric virus of PCV1 and PCV2. In a particular embodiment, a PCV1 virus expressing a capsid protein of PCV2 subtype PCV2b is constructed. As an exemplary process, the inventors first generated an infectious DNA clone of PCV2b subtype, and then constructed a novel chimeric virus, PCV1-2b, containing the immunogenic capsid gene of the PCV2b subtype in the genomic backbone of the non-pathogenic PCV1. The pathogenicity and immunogenicity of the novel chimeric PCV1-2b virus were first evaluated in CD/CD pigs. Subsequently, a challenge and cross-challenge study was performed in conventional pigs to determine the vaccine efficacy of the PCV1-2b chimeric vaccine virus. The inventors demonstrated that the chimeric PCV1-2b vaccine virus is attenuated in pigs and induces protective immunity against PCV2b and cross-protective immunity against PCV2a. Therefore, this new chimeric PCV1-2b virus should be an excellent candidate as a live-attenuated vaccine against both PCV2b and PCV2a infections and PCVAD.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

Example 1

PCV1 and PCV2 Virus Isolates

The PCV1 infectious DNA clone was constructed in previous studies and shown to be non-pathogenic in pigs (Fenaux, M. et al., 2002, Cloned genomic DNA of type 2 porcine circovirus is infectious when injected directly into the liver and lymph nodes of pigs: characterization of clinical disease, virus distribution, and pathologic lesions, J Virol 76:541-51; Fenaux, M. et al. 2004A, supra; Fenaux, M. et al., 2003, supra). PCV2a isolate ISU-40895 (SEQ ID No:1, Genbank accession no. AF264042) was recovered from a pig with PCVAD in an Iowa farm in 1998 (Fenaux, M. et al., 2000, supra) and has been used extensively in PCV2 pathogenicity studies (Fenaux, M. et al., 2002, supra; Fenaux, M. et al., 2004, supra; Fenaux, M. et al., 2003, supra; Opriessnig, T. et al., 2006, Evidence of breed-dependent differences in susceptibility to porcine circovirus type-2-associated disease and lesions, Vet Pathol 43:281-93; Opriessnig, T. et al., 2006, Effects of the timing of the administration of Mycoplasma hyopneumoniae bacterin on the development of lesions associated with porcine circovirus type 2, Vet Rec 158:149-54; Opriessnig, T. et al., 2004, Experimental reproduction of postweaning muitisystemic wasting syndrome in pigs by dual infection with Mycoplasma hyopneumoniae and porcine circovirus type 2, Vet Pathol 41:624-40; Opriessnig, T. et al., 2003, Effect of vaccination with selective bacterins on conventional pigs infected with type 2 porcine circovirus, Vet Pathol 40:521-9). PCV2a-40895 is capable of causing PCVAD microscopic lesions and clinical disease in experimental conditions (Opriessnig, T. et al., 2006, supra; Opriessnig, T. et al., 2004, Effect of porcine parvovirus vaccination on the development of PMWS in segregated early weaned pigs coinfected with type 2 porcine circovirus and porcine parvovirus, Vet Microbiol 98:209-20; Opriessnig, T. et al., 2004, supra). The PCV2b strain used in the study was confirmed to be an authentic PCV2b subtype by sequencing of the entire viral genome (SEQ ID No:2, Genbank accession no. GU799576). The genomic DNA of the PCV2b was used as the source for the construction of the infectious DNA clones of PCV2b as well as the chimeric PCV1-2b infectious DNA clone. The pathogenicity of the PCV2b virus was not determined, prior to the present invention, in experimental infections.

Example 2

Generation of Infectious DNA Clones of PCV2b and Chimeric PCV1-2b

The method for the construction of the infectious DNA clone of PCV2a-40895 has been reported previously (Fenaux, M. et al., 2002, supra), and a similar approach was used in the present invention to produce an infectious DNA clone of PCV2b (FIG. 1a). Briefly, the full-length genome of PCV2b was amplified by PCR using a pair of primers A (SEQ ID No:3) and B (SEQ ID No:4)(Table 1) with an overlapping region containing the Sac II restriction enzyme site that is present in all PCV2 strains. The PCR product was then digested with Sac II (New England Biolabs) and ligated into pBluescript II SK(+) (pBSK+) (Stratagene) to produce an infectious DNA clone of PCV2b.

To produce the chimeric PCV1-2b infectious DNA clone, overlap-extension PCR was used to replace the PCV1 capsid gene in the backbone of a PCV1 infectious clone with the capsid gene from PCV2b (FIG. 1b). The full-length chimeric PCV1-2b genome was assembled from three overlapping PCR fragments (Table 1). Each amplicon was generated using Platinum® Taq HiFi mastermix (Invitrogen) with the same amplification parameters (95° C. 3 min.; 40 cycles of 95° C. 30 sec, 55° C. 30 sec, 68° C. 1 min). PCR products were purified using the QIAquick® Gel Extraction Kit (Qiagen). Fusion PCRs consisting of two steps were used to assemble the chimeric PCV1-2b DNA clone: an assembly reaction without primers using 50 ng of each fragment as template (20 cycles of 95° C. 30 sec, 55° C. 30 sec, 68° C. 1 min) followed by amplification using outer primers (40 cycles of 95° C. 30 sec, 55° C. 30 sec, 68° C. 1 min). The 1,043 bp fragment amplified from a PCV1 clone with primers G (SEQ ID No:9) and H (SEQ ID No:10) (Table 1) was first fused with the 718 bp fragment containing the entire capsid gene amplified from PCV2b with primers C (SEQ ID No:5) and D (SEQ ID No:6) (Table 1). The 122 bp fragment amplified from PCV1 with primers E (SEQ ID No:7) and F (SEQ ID No:8) (Table 1) was then added, resulting in a complete chimeric PCV1-2b genome flanked by Kpn I restriction sites. The chimeric fusion product was subsequently digested with Kpn I (New England Biolabs), and cloned into pBSK+. Monomeric DNA clones were completely sequenced to confirm that no unwanted mutations had been introduced during PCR amplification steps.

Example 3

Dimerization of PCV2b and PCV1-2b DNA Clones

Previous studies showed that dimmerized PCV2a clones with two copies of full-length PCV2a genome ligated head-to-tail in tandem are more efficient in generating infectious virus in both in vitro transfection in PK-15 cells and in vivo transfection in pigs (Fenaux, M. et al., 2002, supra; Fenaux, M. et al., 2004A, supra; Fenaux, M. et al., 2003, supra). Therefore, in the present invention both PCV2b and PCV1-2b clones were dimmerized to produce more robust and efficient infectious clones. Briefly, plasmid DNAs containing PCV2b and PCV1-2b monomeric genomes were extracted using the QIAprep® Spin Miniprep kit (Qiagen). The purified plasmid DNA was linearized using Sca I (New England Biolabs) and subjected to partial digestion with Kpn I by incubation at 37° C. for 30 sec to generate two fragments of approximately 3,100 and 3,700 bp which were then purified by gel extraction. The two fragments were combined and ligated using T4 DNA ligase (Promega) to generate the tandem dimerized infectious DNA clones for both PCV2b and PCV1-2b.

Example 4

Viability Testing of PCV2b and PCV1-2b Infectious DNA Clones in PK-15 Cells

The viability and infectivity of the PCV2b and chimeric PCV1-2b DNA clones were tested in vitro after transfection using an indirect fluorescent assay (IFA) as previously described (Fenaux, M. et al., 2002, supra). Briefly, 6.5 µg of each dimerized DNA clone was added to 1,250 µl OPTIMEM® media (Invitrogen) and 6.25 µl PLUS™ Reagent (Invitrogen) and incubated at room temperature for 5 min. After addition of 16 µl Lipofectamine® LTX (Invitrogen), the mixture was incubated at room temperature for 30 min., followed by addition of 250 µl OPTIMEM® media. T25 cell culture flasks (Corning) containing PK-15 cells at 60-70% confluency were washed with MEM media (Invitrogen), the transfection mixture was added, and the flasks were then incubated for 6 hrs at 37° C. After incubation, 8 ml growth media (MEM containing 10% fetal bovine serum and 2× antibiotic/antimycotic solution [Invitrogen]) was added to each flask and incubated for additional 72 hrs at 37° C. The transfected cells in each T25 flasks were then frozen and thawed three times at −80° C., and cell lysates were centrifuged at 2,500×g at 4° C. for 10 min to remove cellular debris. The supernatants were harvested and used to infect fresh PK-15 cells seeded in 48-well plates (BD-Falcon) at 50% confluency. After addition of 100 µl of transfection supernatant per well, plates were incubated for 1 hr at 37° C., followed by addition of 500 µl growth media to each well and incubation for 72 hrs at 37° C. Capsid proteins in the nuclei of infected PK-15 cells were visualized using IFA as previously described (Fenaux, M. et al. 2002, supra). Briefly, cells were fixed using 80% acetone in PBS at 4° C. for 30 min, washed one time with PBS buffer, and incubated with a 1:1,000 dilution of a PCV2 mono-specific mouse monoclonal antibody (Rural Technologies, Inc.; Brookings, S. Dak.) at 37° C. for 45 min. After washing three times with PBS buffer, the cells were incubated with a 1:50 dilution of FITC-labeled secondary goat anti-mouse IgG (KPL) at 37° C. for 45 min. After washing with PBS buffer, the cells were then covered with Fluoromount-G® (Southern Biotech) and examined under a fluorescent microscope.

PCV2b and chimeric PCV1-2b DNA clones are infectious when transfected into PK-15 cells: Full-length single copy and tandemly-dimerized DNA clones of PCV2b and chimeric PCV1-2b were constructed and verified by full-length sequencing. Transfection of PK-15 cells with dimers of both DNA clones resulted in the production of infectious progeny virions as detected by IFA with PCV2 capsid-specific monoclonal antibodies. The infectious titers of both PCV2b and chimeric PCV1-2b virus stocks were approximately $10^{4.5}$ $TCID_{50}$/ml.

Example 5

Generation and Titration of Infectious PCV2a, PCV2b, and PCV1-2b Virus Stocks

To prepare inocula for the in vivo pig studies, infectious virus stocks were generated for PCV2a-40895, PCV2b, and PCV1-2b by transfection of PK-15 cells in T25 flasks with dimerized infectious DNA clones (see above) (Fenaux, M. et al. 2002.supra; Fenaux, M. et al. 2003, supra). The titration of these infectious virus stocks by IFA was performed essentially as described previously (Fenaux, M. et al. 2002, supra). Briefly, PK-15 cells were seeded in 48-well plates (BD-Falcon) at 60% confluency and incubated for 3 hrs at 37° C. Serial ten-fold dilutions of each of the virus stocks were produced in MEM, and each dilution was inoculated onto four separate wells with 100 µl per well. Plates were incubated for 1 hr at 37° C., followed by addition of 500 µl growth media to each well and continued incubation for 72 hrs at 37° C. Positive signals in the nuclei of infected cells were visualized in each well using IFA (see above). The 50% tissue culture infective dose ($TCID_{50}$) per ml was calculated according to the method of Reed & Muench.

Example 6

Experimental Design for the Pathogenicity Study of PCV2b and Chimeric PCV1-2b in Caesarean-Derived Colostrum-Deprived (CD/CD) Pigs CD/CD pigs are considered to be a superior model system for the study of PCV2 pathogenicity since characteristic pathological lesions and clinical PCVAD can be reproduced in this model (Allan, G. et al., 2003, supra; Bolin, S. R. et al., 2001, supra; Harms, P. A. et al., 2001, supra; Kennedy, S. et al., 2000, supra; Tomas, A. et al., 2008, supra). To determine the pathogenicity of the chimeric PCV1-2b virus and compare it to the wildtype PCV2b virus, a total of 30 CD/CD pigs (Struve Labs, Manning, Iowa), approximately 9 weeks of age, were randomly assigned to three groups in rooms of 10 animals each. Prior to inoculation, each pig was weighed, bled, and confirmed to be negative for the presence of PCV2 antibodies. Group 1 pigs were each mock-inoculated with 3 ml PBS buffer (2 ml intranasally and 1 ml intramuscularly) and served as uninfected controls. Pigs in group 2 were each inoculated with 3 ml of inoculum containing $2 \times 10^{4.5}$ $TCID_{50}$ chimeric PCV1-2b virus (2 ml intranasally and 1 ml intramuscularly). Pigs in group 3 were each similarly inoculated with $2 \times 10^{4.5}$ $TCID_{50}$ wildtype PCV2b virus. Blood samples were collected prior to inoculation, and weekly thereafter from each pig until necropsy at 21 or 42 days post-inoculation (dpi). At 21 dpi, five randomly assigned pigs from each group were necropsied. The remaining five pigs in each group were necropsied at 42 dpi.

Example 7

Experimental Design for the Pathogenicity Study of PCV2b and Chimeric PCV1-2b in Caesarean-Derived Colostrum-Deprived (CD/CD) Pigs CD/CD pigs are considered to be a superior model system for the study of PCV2 pathogenicity since characteristic pathological lesions and clinical PCVAD can be reproduced in this model (Allan, G. et al., 2003, supra; Bolin, S. R. et al., 2001, supra; Harms, P. A. et al., 2001, supra; Kennedy, S. et al. 2000, supra; Tomas, A. et al. 2008, supra). To determine the pathogenicity of the chimeric PCV1-2b virus and compare it to the wildtype PCV2b virus, a total of 30 CD/CD pigs (Struve Labs, Manning, Iowa), approximately 9 weeks of age, were randomly assigned to three groups in rooms of 10 animals each. Prior to inoculation, each pig was weighed, bled, and confirmed to be negative for the presence of PCV2 antibodies. Group 1 pigs were each mock-inoculated with 3 ml PBS buffer (2 ml intranasally and 1 ml intramuscularly) and served as uninfected controls. Pigs in group 2 were each inoculated with 3 ml of inoculum containing $2 \times 10^{4.5}$ $TCID_{50}$ chimeric PCV1-2b virus (2 ml intranasally and 1 ml intramuscularly). Pigs in group 3 were each similarly inoculated with $2 \times 10^{4.5}$ $TCID_{50}$ wildtype PCV2b virus. Blood samples were collected prior to inoculation, and weekly thereafter from each pig until necropsy at 21 or 42 days post-inoculation (dpi). At 21 dpi, five randomly assigned pigs from each group were necropsied. The remaining five pigs in each group were necropsied at 42 dpi.

Chimeric PCV1-2b virus is attenuated in CD/CD pigs whereas the wildtype PCV2b virus induces pathological lesions and clinical diseases characteristic of PCVAD: To definitively assess the pathogenic potential of the chimeric PCV1-2b virus, the pathogenicity study was conducted in a CD/CD pig model which has been shown to be the most reproducible and highly sensitive PCVAD disease model (Allan, G. et al., 2003, supra; Bolin, S. R. et al., 2001, supra; Harms, P. A. et al., 200,1 supra; Kennedy, S. et al. 2000, supra).

Clinical Signs and Gross Lesions:

CD/CD pigs experimentally-inoculated with chimeric PCV1-2b virus or PBS buffer had no apparent clinical signs of PCVAD throughout the study, whereas experimental inoculation of CD/CD pigs with wildtype PCV2b resulted in the PCVAD-associated death or early euthanasia in four of the 10 PCV2b-infected pigs: one pig died at 18 dpi, another died at 27 dpi, and two other pigs had to be euthanized at 34 dpi due to progressive weight loss.

Pigs from each of the three treatment groups had similar weight gain through 21 dpi, but the wildtype PCV2b-infected pigs had a decrease in weight gain in four of the five pigs after 21 dpi (three of which died or were euthanized early due to weight loss). Macroscopic lung lesions were not observed in pigs inoculated with the chimeric PCV1-2b virus, whereas the three PCV2b-inoculated pigs necropsied at 27 dpi and 34 dpi displayed moderate lung lesions. Lymph nodes were enlarged in both PCV1-2b and PCV2b infected pigs compared to the PBS controls. However, the number of pigs with enlarged lymph nodes and the magnitude of enlargement was less in PCV1-2b-infected pigs than in wildtype PCV2b pigs (data not shown).

Microscopic Lesions:

Microscopic lesions were analyzed by treatment in two groups: all pigs necropsied at 21 dpi or before (including the PCV2b-infected pig that died at 18 dpi), and all pigs necropsied at 42 dpi (including the three PCV2b-infected pigs that died or were euthanized at 27 dpi and 34 dpi).

Microscopic lesions in lung, liver, thymus, heart, kidney, ileum, colon, lymph nodes, spleen, and tonsil are summarized in Table 2. As expected, there were no remarkable microscopic lesions in pigs inoculated with PBS buffer. Characteristic PCV2-associated microscopic lesions in lymphoid tissues in pigs inoculated with chimeric PCV1-2b virus were decreased in incidence and severity compared to the pigs experimentally inoculated with the wildtype PCV2b at both 21 and 42 dpi (Table 2). Microscopic lesions in other non-lymphoid tissues included mild to severe infiltration with lymphocytes and macrophages (Table 2). Lesions in the small and large intestine were found almost exclusively in wildtype PCV2b-infected pigs.

Figure 3:
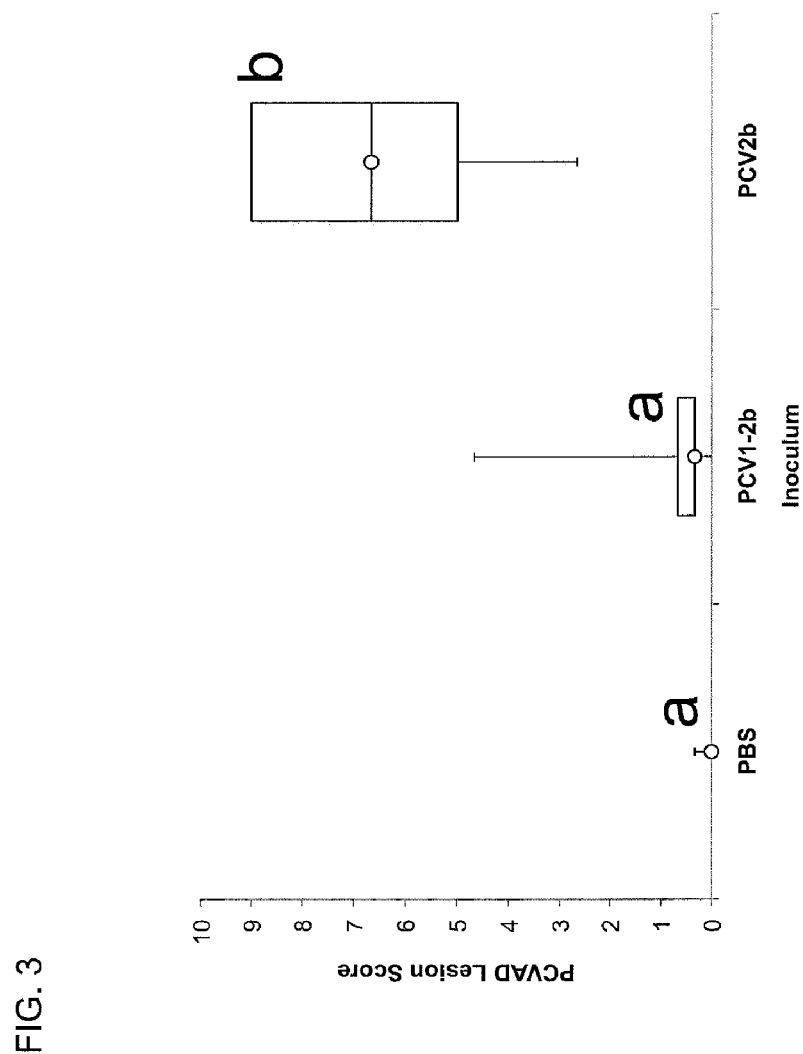
Figure 4:
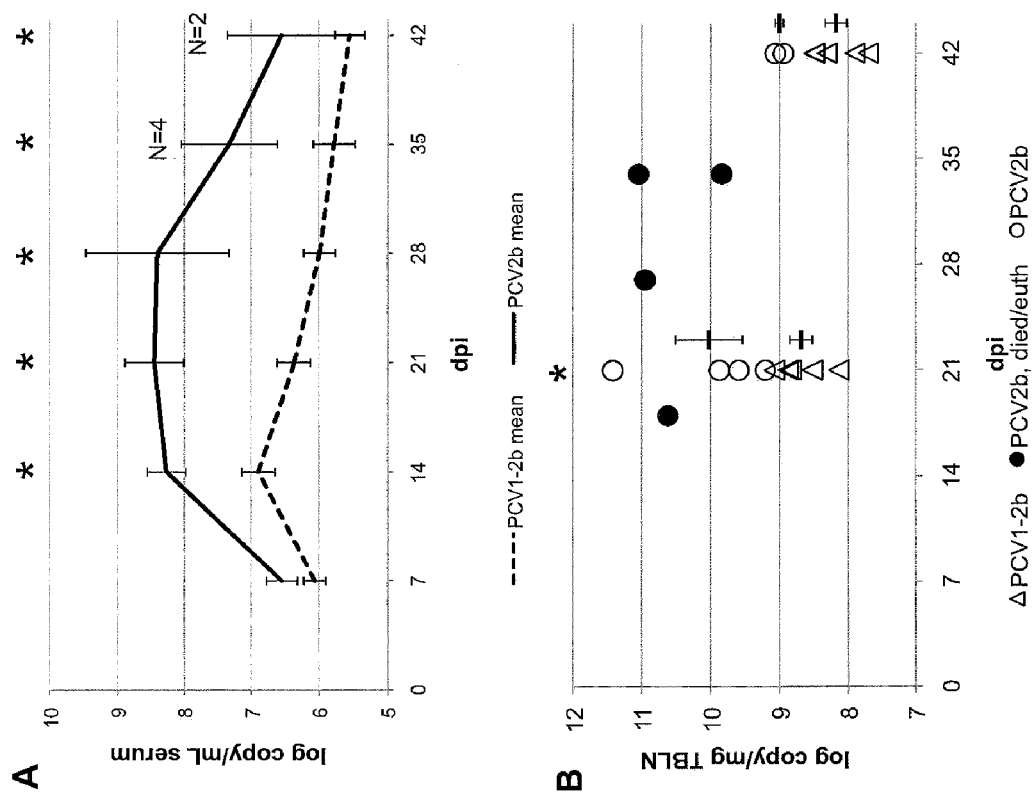

The mean group overall lymphoid lesion score in pigs inoculated with the chimeric PCV1-2b virus was significantly (p=0.045) lower than that in pigs inoculated with the wildtype PCV2b virus and was not different from pigs inoculated with PBS buffer at 21 dpi (FIG. 3).

Figure 2:
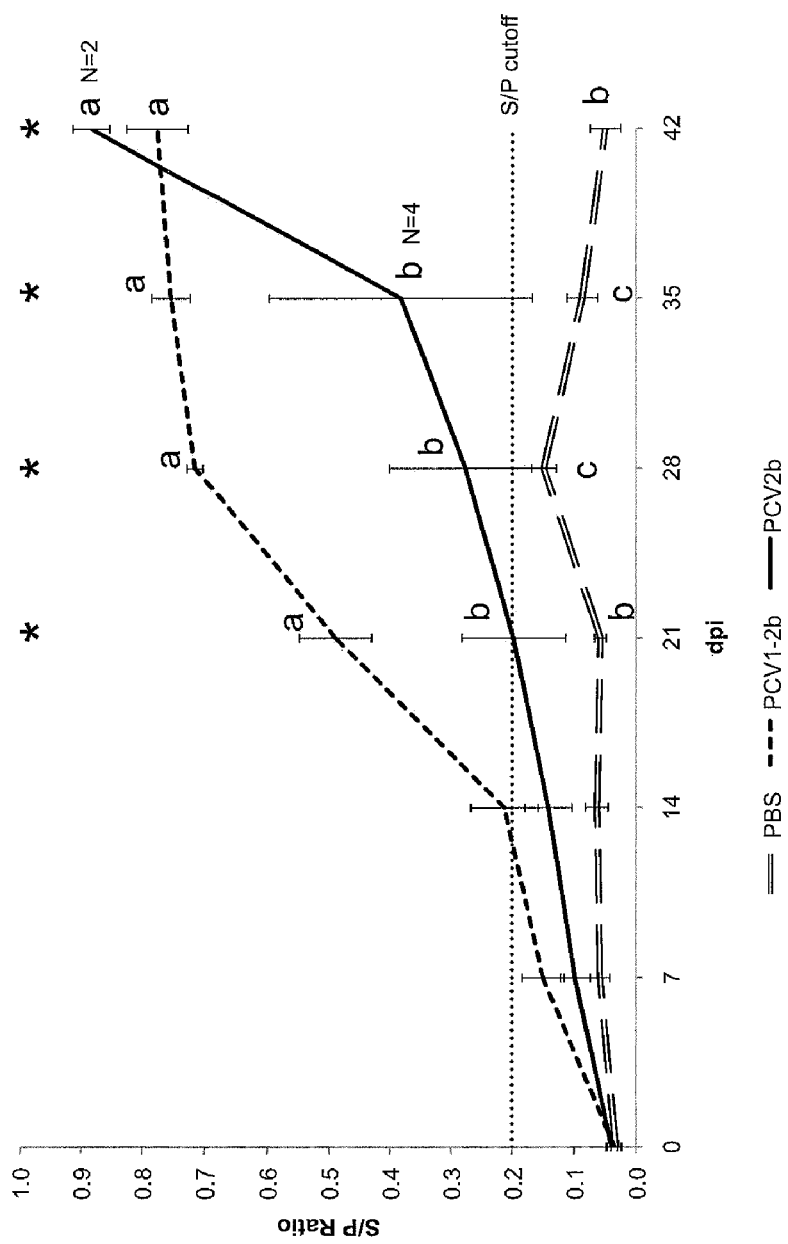

PCV2 Serology:

Serum samples taken from pigs that died or were euthanized early were analyzed along with those from the next scheduled necropsy (e.g. serum from the pig that died at 18 dpi was included in the analysis of samples from 21 dpi necropsy). PCV2 capsid-specific IgG antibodies were detected in the sera of some PCV1-2b-infected pigs as early as 7 dpi, with seroconversion in 9/10 pigs by 21 dpi (FIG. 2). The PCV2 IgG antibody titers in chimeric PCV1-2b virus-inoculated pigs plateaued by 28 dpi and remained high through the end of the study at 42 dpi. In pigs experimentally-inoculated with wildtype PCV2 virus, the seroconversion was less uniform: only 3/10 pigs were seropositive by 21 dpi, and 5/10 pigs had no detectable seroconversion in the study. However, only $\frac{2}{5}$ PCV2b-infected pigs survived to the scheduled necropsy at dpi 42, and both of them did seroconvert at 28 dpi, with increasing IgG antibody titers towards the end of the study. Of the pigs that died or were euthanized early due to clinical PCVAD, only $\frac{1}{4}$ had detectable PCV2-specific antibody at any time, and none had detectable serum anti-PCV2 antibody on the day they were necropsied. No PCV2 capsid-specific antibodies were detected in any of the PBS buffer-inoculated pigs throughout the study.

Prevalence and Amount of PCV2-Specific Antigen in Tissues by IHC:

Prevalence and mean group amounts of PCV2 antigen in the different tissues are summarized in Table 3. All pigs necropsied at 21 dpi or before (including the PCV2b-infected pig that died at 18 dpi) were analyzed together, and all pigs necropsied at 42 dpi (including the three PCV2b-infected pigs that died or were euthanized at 27 dpi and 34 dpi) were analyzed together. In general, the incidence and amount of PCV2 antigen were less in pigs inoculated with the chimeric PCV1-2b virus compared to the pigs inoculated with the wildtype PCV2b virus (Table 3). There was a single PCV1-2b-inoculated pig that accounted for the positive results in all 21 dpi tissues except the tonsil, where four of five pigs were positive. Tissues from PCV1-2b-inoculated pigs were mostly negative at 42 dpi, with the exception of the lymph nodes, in which low amounts of PCV2 antigen were detected in four of five pigs.

PCV2 Viremia and Serum Viral Loads:

The PCV2 viral load in the sera of infected animals was determined using a modified qPCR assay that amplifies part of the PCV2b capsid gene and the qPCR assay is known to work with both PCV2b and PCV1-2b (Yang, Z. Z. et al., 2007, Detection of PCV2 DNA by SYBR Green 1-based quantitative PCR. J Zhejiang Univ Sci B 8:162-9). All serum samples taken prior to inoculation at day 0 and from PBS buffer-inoculated pigs throughout the study were confirmed to have no detectable PCV2 DNA. Serum samples taken from pigs that died or were necropsied early due to PCVAD disease were analyzed along with those from the next scheduled necropsy (e.g. serum from pig that died at 18 dpi was included in the analysis of samples from 21 dpi).

Figure 6:
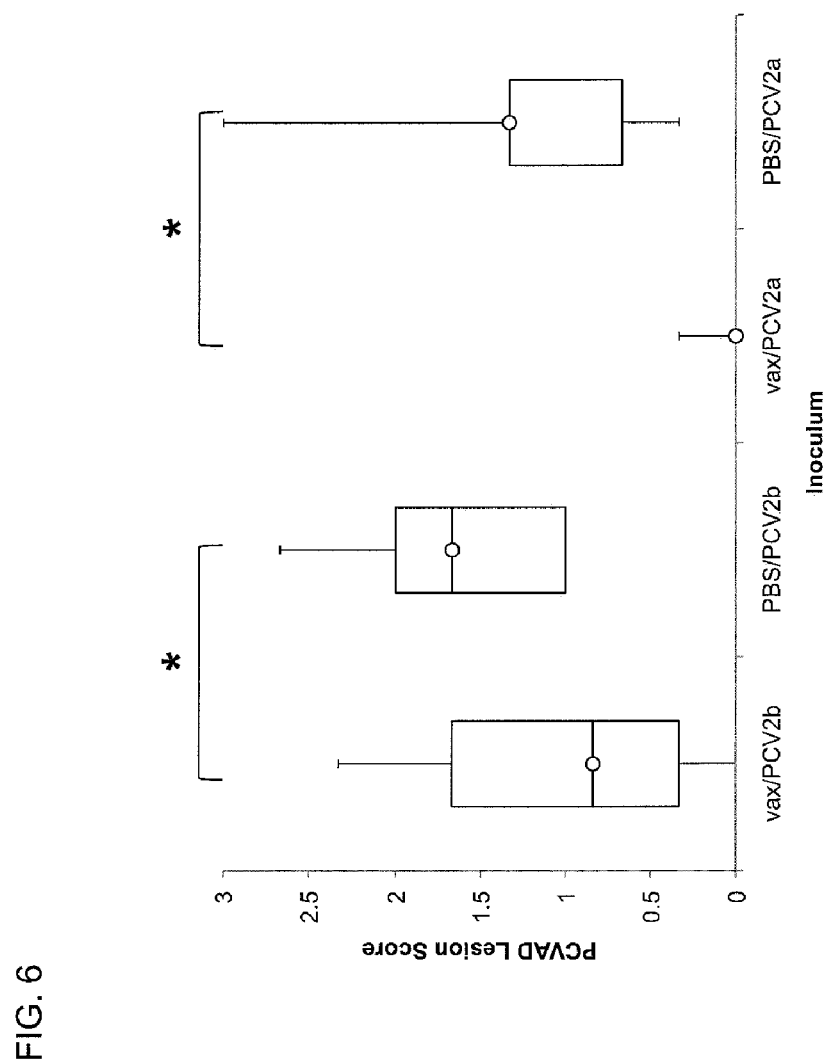

The serum viral loads present in pigs inoculated with the chimeric PCV1-2b virus were significantly ($p \leq 0.009$) lower than the serum viral loads in PCV2b-inoculated pigs from 14 dpi through the end of the study (FIG. 4*a*). The mean serum viral loads peaked at $10^7$ genomic copies/ml at 14 dpi in PCV1-2b-infected pigs, and steadily decreased towards the end of the study. The maximum value achieved for any individual PCV1-2b-infected pig was $10^8$ genomic copies/ml at 14 dpi. In contrast, the mean serum viral loads in PCV2b-infected pigs remained above $10^8$ genomic copies/ml from 14 dpi until after 28 dpi, with $10^{12}$ being the maximum value achieved by an individual pig. The four pigs that died early or were euthanized due to PCVAD had higher levels of serum viral loads than the other PCV2b-inoculated pigs. After 7 dpi, PCV2b-infected pigs had at least ten-fold greater viral genomic copies per ml of serum than the PCV1-2b-infected pigs, and one hundred-fold greater at 21 dpi and 28 dpi.

PCV2 Viral Load in Lymphoid Tissues:

The amount of PCV2 viral DNA in the TBLN tissues collected at necropsy of each pig was determined using the same qPCR assay as above. All TBLN tissue samples from PBS buffer-inoculated pigs were confirmed to be negative for PCV2 DNA. In order to enable a meaningful comparison of group mean viral loads at 21 dpi and 42 dpi, pigs that died early or were euthanized due to PCVAD disease were tested but not included in the analysis. The viral load present in each mg of TBLN tissue was found to be significantly lower in PCV1-2b-inoculated pigs than in PCV2b-inoculated pigs at 21 dpi ($p=0.005$) (FIG. 4*b*). Pigs that died or were euthanized early due to PCVAD had the highest viral loads in TBLN tissues among all that were tested.

Example 8

Experimental Design for Vaccination and Immunogenicity Study of the Chimeric PCV1-2b Virus in Conventional Specific-Pathogen-Free (SPF) Pigs A total of 40, 3-week-old, cross-breed SPF pigs were purchased from a commercial farm (Virginia Tech Swine Center, Blacksburg, Va.) that is known to be free of PCV, PRUSV, PPV, *M. hyopneumonia*, and swine hepatitis E virus. The piglets were randomly assigned to two groups of 20 pigs each, and housed separately. Prior to inoculation, each pig was weighed, bled, and confirmed to be negative for PCV2 antibodies. Group 1 pigs were each vaccinated intramuscularly (IM) with 1 ml of the chimeric PCV1-2b virus ($10^{3.5}$ $TCID_{50}$ infectious virus per pig). Group 2 pigs were each mock-vaccinated IM with 1 ml PBS buffer and served as unvaccinated controls. All animals were monitored daily for clinical signs, and blood samples were collected prior to inoculation, and weekly thereafter from each pig through 56 days post-vaccination (dpv).

Example 9

Experimental Design for Challenge and Cross-Challenge of Vaccinated Pigs with Wildtype PCV2b Subtype and PCV2a Subtype, Respectively At 56 dpv, the 20 vaccinated pigs were further divided into two groups of 10 pigs each and housed in separate rooms: 10 vaccinated pigs were each challenged with $2\times10^{4.5,}$ $TCID_{50}$ wildtype PCV2b virus (2 ml intranasally and 1 ml IM), and the other 10 vaccinated pigs were each similarly cross-challenged with $2\times10^{4.5,}$ $TCID_{50}$ wildtype PCV2a virus. The 20 unvaccinated control pigs were also further divided into two groups of 10 pigs each, and similarly inoculated with PCV2b and PCV2a, respectively. Blood samples were collected weekly through 21 days post-challenge (dpc) (or 77 dpv), at which time all pigs were necropsied.

Vaccination with chimeric PCV1-2b virus confers protective immunity in conventional pigs against challenge with PCV2b subtype and cross-challenge with PCV2a subtype: Since the chimeric PCV1-2b vaccine is intended for usage in conventional pigs in the field, the inventors thus conducted this vaccine efficacy and challenge study using conventional SPF pigs.

Clinical Signs and Gross Lesions:

None of the pigs developed clinical signs consistent with PCVAD throughout the study, and no difference in weight gain was observed between treatment groups. A single pig assigned to the unvaccinated/PCV2b challenge group died at 2 dpc from bacterial septicemia unrelated to PCVAD, and was not included in the analysis. Upon necropsy, macroscopic lung lesions were not observed in any of the treatment groups. Mild to moderately enlarged lymph nodes were seen in all treatment groups, with no significant differences observed between treatments.

Serology:

All pigs were determined to be negative for antibodies against PCV2, PRRSV, PPV, and SIV prior to the study. PCV2 capsid-specific antibodies were detected in the sera of PCV1-2b-vaccinated pigs as early as 14 dpv, with seroconversion occurred in 15/20 pigs at 21 dpv and 20/20 by 28 dpv (FIG. 5). The PCV2 IgG antibody titers plateaued by 35 dpv and remained high at the time of challenge at 56 dpv. Antibodies to PCV2 were not detected in unvaccinated control pigs until after challenge at 14 dpc (FIG. 5): 10/10 PCV2a-challenged pigs were seropositive, compared to only 2/9 seropositive PCV2b-challenged pigs at 14 dpc. By 21 dpc, 7/9 unvaccinated PCV2b-challenged pigs had seroconverted.

Microscopic Lesions:

After challenge, the incidence and severity of microscopic lesion scores in lymphoid tissues were higher in unvaccinated pigs compared to the vaccinated ones (Table 4). In general, the characteristic lymphoid depletion and histiocytic replacement scores were lower in vaccinated pigs compared to the unvaccinated controls (Table 4). The overall lymphoid lesion score in vaccinated pigs was significantly lower than that in unvaccinated pigs for both PCV2a (p=0.0001) and PCV2b (p=0.04) challenge groups (FIG. 6).

Amount of PCV2 Antigen by IHC in Tissues:

IHC was used to detect PCV2-specific antigens in each tissue type (Table 4). Similarly to the histological lesions, in general the incidence and the amount of PCV2 antigen in tissues were reduced in vaccinated pigs compared to unvaccinated controls (Table 4).

Figure 7:
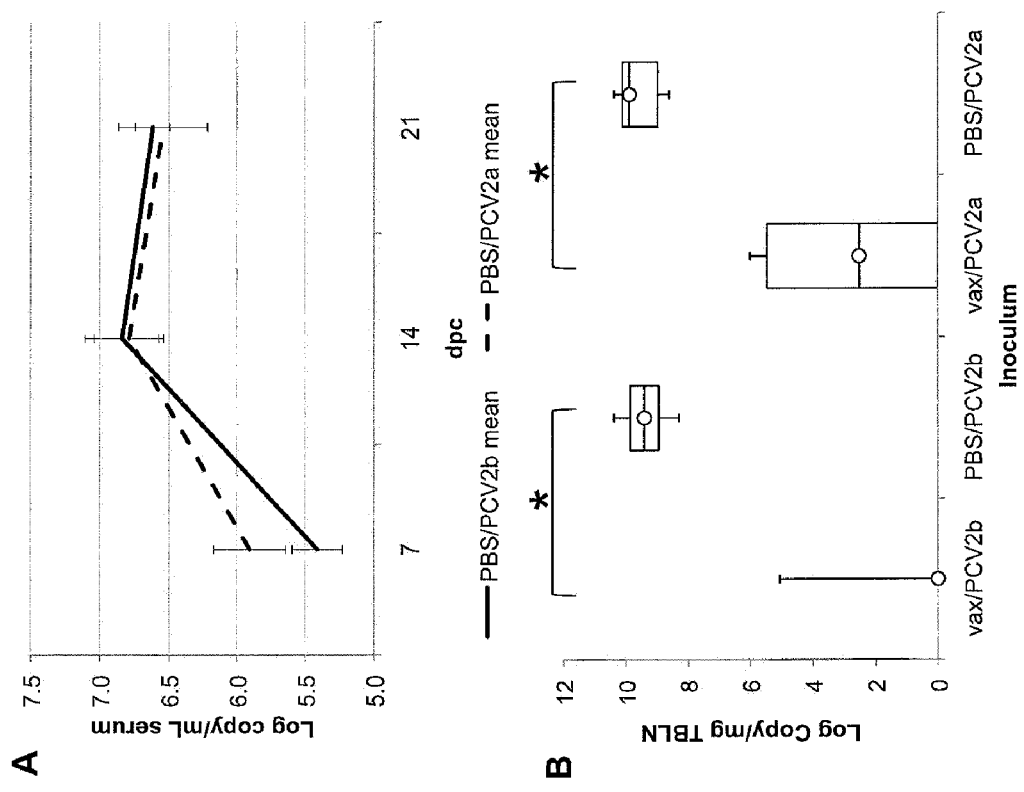

Viremia and Serum Viral Load:

The amounts of PCV2a or PCV2b viral DNA in the serum after challenge were quantified using a modified qPCR assay that is specific for the detection of PCV2a or PCV2b rep gene but is not capable of amplifying the vaccine virus PCV1-2b (Mcintosh, K. A. et al. 2009. Development and validation of a SYBR green real-time PCR for the quantification of porcine circovirus type 2 in serum, buffy coat, feces, and multiple tissues. Vet Microbiol 133:23-33). Serum samples collected prior to challenge at 56 dpv were confirmed to have no detectable PCV2 DNA. There was no detectable PCV2a or PCV2b viremia in vaccinated pigs at any time point post-challenge. In contrast, PCV2a or PCV2b viremia was detected in all unvaccinated pigs at every time point post-challenge (FIG. 7a). There was no statistically significant difference in serum viral load between unvaccinated pigs challenged with PCV2a or PCV2b virus.

PCV2a or PCV2b Viral Load in Lymphoid Tissues:

The amounts of PCV2a or PCV2b viral DNA in the TBLN tissues collected at necropsy are summarized in FIG. 7b. The viral loads in each mg of TBLN tissues were found to be significantly lower in vaccinated pigs compared to unvaccinated ones in both PCV2a (p=0.0001) and PCV2b (p<0.0001) challenge groups (FIG. 7b). Only $1/10$ of the vaccinated and PCV2b challenged pigs had detectable PCV2b viral DNA in the TBLN tissues, with a viral load of $10^5$ genomic copies/mg. Five of ten vaccinated and PCV2a challenged pigs had detectable PCV2a viral DNA in the TBLN tissues, each with a viral load of $10^5$-$10^6$ genomic copies/mg. The viral load in the TBLN tissues of the unvaccinated pigs ranged from $10^8$-$10^{10}$ genomic copies/mg, regardless of PCV2a or PCV2b challenge.

Experimental Materials and Methods

Cells: A subclone of the PK-15 cell line that is free of PCV1 contamination was produced previously by end-point dilution of the PK-15 cells (ATCC CCL-33) (Fenaux, M. et al., 2000, supra; Fenaux, M. et al., 2002, supra). The PCV1-free PK-15 cell line was used for the generation of infectious virus stocks, and for the infectivity titration of the virus stocks used in the present invention.

Serology: ELISA was used to detect anti-PCV2 IgG in each serum sample as previously described (Nawagitgul, P. et al., 2002, Modified indirect porcine circovirus (PCV) type 2-based and recombinant capsid protein (ORF2)-based enzyme-linked immunosorbent assays for detection of antibodies to PCV, Clin Diagn Lab Immunol 9:33-40). Serum samples with sample: positive (S:P) ratios greater than 0.2 were considered to be positive for anti-PCV2 antibodies. All pigs were confirmed to be PCV2 seronegative by ELISA prior to the start of the animal experiments.

Clinical evaluation: Following inoculation, vaccination or challenge, pigs were evaluated daily for clinical signs of PCVAD including wasting, respiratory distress, and behavioral changes such as lethargy and inappetance.

Gross pathology and histopathology: Necropsies were performed at the designated time for the pathogenicity (dpi 21 and 42) or challenge experiment (dpc 21 or dpv 77) on all pigs in a blinded fashion. Estimates of macroscopic lung lesions (ranging from 0-100% of the lung affected) and lymph node size (ranging from 0 [normal] to 3 [four times the normal size]) were made and scored for each pig (Halbur, P. G. et al., 1995, Comparison of the pathogenicity of two US porcine reproductive and respiratory syndrome virus isolates with that of the Lelystad virus, Vet Pathol 32:648-60; Opriessnig, T. et al., 2004, supra).

Sections of lung, lymph nodes (superficial inguinal, mediastinal, tracheobronchial, and mesenteric), tonsil, heart, thymus, ileum, kidney, colon, spleen, and liver were collected during each necropsy and fixed in 10% neutral-buffered formalin and processed routinely for histological examination and immunohistochemistry (IHC). Also, samples of tracheobronchial lymph node (TBLN) were collected from each pig for DNA extraction and quantification of viral genomes by real-time PCR. Microscopic lesions in the lungs, heart, liver, kidney, ileum, and colon were scored in a blinded manner, as described previously (Opriessnig, T. et al., 2004, supra). Lymphoid tissues including lymph nodes, spleen, and tonsil were evaluated based on lymphoid depletion and histiocytic replacement of follicles, ranging from 0 (normal) to 3 (severe) (Opriessnig, T. et al., 2004, supra).

Immunohistochemistry (IHC): IHC for detection of PCV2-specific antigen was performed on formalin-fixed, paraffin-embedded sections of lung, lymph nodes (superficial inguinal, mediastinal, tracheobronchial, and mesenteric), tonsil, heart, thymus, ileum, kidney, colon, spleen, and liver using a rabbit polyclonal antiserum (Sorden, S. D. et al. 1999. Development of a polyclonal-antibody-based immunohistochemical method for the detection of type 2 porcine circovirus in formalin-fixed, paraffin-embedded tissue. J Vet Diagn Invest 11:528-30). The scores of PCV2 antigen in each tissue were estimated in a blinded fashion and the scores ranged from 0 (no antigen) to 3 (greater than 50% lymphoid follicles contained cells with positive PCV2 antigen staining in lymphoid tissues or high amount of PCV2 antigen in other tissue sections) (Opriessnig, T. et al., 2004, supra).

Overall microscopic lymphoid lesion scores: The average scores of the overall microscopic lymphoid lesions were calculated for each pig as described previously (Opriessnig, T. et al., 2004, supra). These lesion scores are based on the combined lymphoid depletion (LD), histiocytic replacement (HR), and PCV2 antigen present in the lymphoid tissues as determined by IHC.

Quantitative real-time PCR to determine viral DNA loads: Total DNA was extracted from serum samples using the QIAamp® DNA minikit (Qiagen Inc) according to the "blood and body fluids" protocol supplied by the manufacturer. TBLN tissues collected during necropsies were homogenized to produce a 10% tissue homogenate suspension in sterile PBS buffer, and total DNA was extracted using the QIAamp® DNA minikit with the "tissue" protocol supplied by the manufacturer (Qiagen Inc). All TBLN DNA extracts were diluted at least 1:100 in sterile $H_2O$ in order to eliminate background fluorescence from SYBR® green binding to porcine genomic DNA. Due to the extremely high viral DNA concentrations in some samples, some serum and TBLN extracts were diluted as much as $1:10^6$ in order to bring them within the linear range of qPCR detection. Two SYBR® green I-based qPCR assays were modified for use in the present invention to quantify the PCV2 genomes present in TBLN and serum DNA extracts (Mcintosh, K. A. et al., 2009, Development and validation of a SYBR® green real-time PCR for the quantification of porcine circovirus type 2 in serum, buffy coat, feces, and multiple tissues, Vet Microbiol 133:23-33; Yang, Z. Z. et al., 2007, supra).

In the CD/CD pig pathogenicity study, the inventors utilized a previously published qPCR assay that amplifies part of PCV2b capsid gene to quantify viral genomes present in serum and TBLN (Yang, Z. Z. et al., 2007, supra).

The protocol was modified to enable the use of the Sensimix® SYBR and fluorescein kit (Quantace). Each 25 µl reaction contained 200 nM each primer (P1 (SEQ ID No:11): 5'-ATAACCCAGCCCTTCTCCTACC-3'); P2 (SEQ ID No:12): 5'-GGCCTACGTGGTCTACATTTCC-3'), 200 µM dNTP, 3 mM MgCl$_2$, and 5 µl DNA extract. Triplicate reactions were run for each sample in MyiQ™ qPCR thermocycler (BioRad) using a modified program (95° C. 10 min.; 35 cycles of 95° C. 15 sec, 59° C. 30 sec, 72° C. 30 sec). Viral genomes were quantified against duplicate standards of PCV2b infectious DNA clone using the relative $C_t$ method, with a 6-log linear range of quantification ($10^3$-$10^8$ copies).

In the challenge and cross-challenge conventional SPF pig study, the inventors used a previously published qPCR assay that amplifies a highly conserved region of PCV2 replicase gene region to quantify the amounts of viral genomes present in serum and TBLN tissues (Mcintosh, K. A. et al., 2009, supra). This assay does not detect the chimeric PCV1-2b vaccine virus used in the vaccination, and thus allowing for accurate quantification of the challenge PCV2a or PCV2b viruses only. This protocol was modified to enable the use of the Sensimix® SYBR and fluorescein kit. Each 25 µl reaction contained 200 nM each primer (PCV2-83F (SEQ ID No:13): 5'-AAAAGCAAATGGGCTGCTAA-3'; PCV2-83R (SEQ ID No:14): 5'-TGGTAACCATCCCACCACTT-3'), 200 µM dNTP, 5 mM MgCl$_2$, and 5 µl DNA extract. Triplicate reactions for each sample were run in a MyiQ™ qPCR thermocycler using a modified program (95° C. 10 min.; 35 cycles of 95° C. 15 sec, 60° C. 15 sec, 72° C. 15 sec). Viral DNA genomes were quantified against duplicate standards of PCV2b infectious DNA clone using the relative $C_t$ method, with a 5-log linear range of quantification ($5\times10^2$-$5\times10^6$ copies).

Sequence confirmation of virus detected by qPCR: TBLN tissues DNA extracts from selected pigs of each group were tested to confirm the virus detected by qPCR was the same virus that was inoculated into pigs at the start of each study. PCV1-2b in the CD/CD pathogenicity study was confirmed by PCR amplification and partial sequencing using primers specific for PCV1-2b (PCV2F (SEQ ID No:15): 5'-TGTT-GAAGATGCCATTTTTCC-3'; PCV1R (SEQ ID No:16): 5'-GAGGAGTTCTACCCTCTTCC-3'). PCV2a and PCV2b were amplified and sequenced using primers specific for PCV2 (PCV2F (SEQ ID No:17): 5'-TGTTGAAGATGC-CATTTTTCC-3'; PCV2R (SEQ ID No:18): 5'-GAGGTGT-TCGTCCTTCCTCA-3').

Statistical Analysis: Serology and serum qPCR were analyzed using repeated measures analysis of variance (ANOVA). TBLN qPCR from the CD/CD pathogenicity study was analyzed using simple ANOVA. For all the ANOVA models simple effects comparisons were investigated using the slice option of the Glimmix procedure followed by Tukey's procedure for multiple comparisons. TBLN qPCR results from the challenge study were analyzed using the exact Wilcoxon 2-sample test. Scores from lymphoid lesions, histopathology lesions, and IHC from both experiments were assessed with the exact Kruskal-Wallis one way ANOVA, followed by the exact Wilcoxon 2-sample test for the 2-way comparisons of interest. The 2-way comparisons were adjusted for multiple comparisons using Bonferroni's procedure. Statistical significance was set to alpha=0.05. All analyses were performed using commercially available software (SAS version 9.2, Cary, N.C., USA).

The inventors have previously developed an inactivated vaccine, Suvaxyn PCV2® One Dose™, based on a chimeric virus made from the PCV2a subtype (Fenaux, M. et al. 2004, supra; Fenaux, M. et al. 2003, supra) and this killed vaccine has been effective and is currently available on the global market. By using a similar strategy, in this present study the inventors first developed a novel chimeric virus PCV1-2b with the capsid gene of the PCV2b subtype cloned in the genomic backbone of the non-pathogenic PCV1. The use of this chimeric PCV1-2b virus as a live-attenuated new generation vaccine against PCV2 and PCVAD was thoroughly investigated in CD/CD and conventional pig models.

For use of the chimeric PCV1-2b virus as a live-attenuated vaccine, it is important to ascertain that the vaccine virus is attenuated. Though PCV2 alone rarely causes full-spectrum clinical disease in experimental models, the use of CD/CD pigs has resulted in successful reproduction of clinical PCVAD (Allan, G. et al., 2003, supra; Bolin, S. R. et al., 2001, supra; Harms, P. A. et al., 2001, supra; Kennedy, S. et al., 2000, supra; Tomas, A. et al., 2008, supra). Therefore, in the present invention in order to definitively determine the pathogenicity of the chimeric PCV1-2b virus and compare it to its parental wildtype PCV2b virus, the inventors chose the CD/CD pig model for the pathogenicity study. As expected, the wildtype PCV2b alone caused severe clinical PCVAD in CD/CD pigs, resulting in the death or early euthanasia due to clinical manifestation of PCVAD in 4/10 PCV2b-infected pigs. This is consistent with previous studies that have shown 25% mortality and significant clinical PCVAD in PCV2-infected CD/CD pigs (Allan, G. et al., 2003, supra; Bolin, S. R. et al., 2001, supra; Harms, P. A. et al., 2001, supra). The overall lymphoid lesion scores for PCV2b-infected pigs were consistent with moderate-to-severe systemic PCVAD (Opriessnig, T. et al. 2007, supra). The generally accepted threshold for viremia in severe PCVAD cases is $10^7$ viral genomic copies per ml of serum, though host variation prevents a single definitive diagnostic cut-off (Brunborg, I. M. et al., 2004, Quantitation of porcine circovirus type 2 isolated from serum/plasma and tissue samples of healthy pigs and pigs with postweaning muiti-systemic wasting syndrome using a TaqMan-based real-time PCR, J Virol Methods 122:171-8; Olvera, A. et al., 2004, Comparison of porcine circovirus type 2 load in serum quantified by a real time PCR in postweaning muitisystemic wasting syndrome and porcine dermatitis and nephropathy syndrome naturally affected pigs, J Virol Methods 117:75-80; Segales, J. et al., 2005, Quantification of porcine circovirus type 2 (PCV2) DNA in serum and tonsillar, nasal, tracheobronchial, urinary and faecal swabs of pigs with and without postweaning muitisystemic wasting syndrome (PMWS), Vet Microbiol 111:223-9). By 21 dpi, 9/10 PCV2b-infected pigs were above this threshold, compared to only 1/10 chimeric PCV1-2b virus-infected pigs. The 4 pigs that died or were euthanized earlier due to PCVAD all had higher PCV2 DNA viral loads in serum and lymphoid tissues but had no detectable PCV2 IgG antibodies, indicating that these PCV2b-infected pigs died because of insufficient immune responses and higher level of virus replication. This result is consistent with a previously reported correlation between low antibody response and increased severity of PCVAD (Meerts, P. et al., 2006, Correlation between the presence of neutralizing antibodies against porcine circovirus 2 (PCV2) and protection against replication of the virus and development of PCV2-associated disease, BMC Vet Res 2:6). The data clearly demonstrated that the PCV2b subtype used in the present invention is highly virulent.

The chimeric PCV1-2b virus was found to be significantly attenuated in the CD/CD pig model, despite the fact that the CD/CD pigs were inoculated with a dose that is at least 20-fold higher than the normal vaccination dose (Fenaux, M. et al., 2004, supra). Attenuation of chimeric PCV1-2b virus was clearly demonstrated by all quantitative and qualitative parameters that were used to compare the chimeric PCV1-2b and the wildtype PCV2b viruses. There was no mortality or morbidity seen in pigs infected with the chimeric PCV1-2b virus, compared to death and wasting seen in about half of the PCV2b-infected pigs. Microscopic lesion scores and the amounts of PCV2-specific antigen in lymphoid tissues were significantly less in the chimeric PCV1-2b-infected pigs than in pigs infected with the wildtype PCV2b, indicating that the chimeric PCV1-2b virus causes only subclinical infection. Overall, the lymphoid lesion scores in chimeric PCV1-2b-infected pigs were not significantly different from the control pigs inoculated with PBS buffer. Additionally, lower PCV2b viral load in the serum and lymphoid tissues directly correlate to the significantly less characteristic lesions or disease severity in the chimeric PCV1-2b-infected pigs, as observed in previous studies (Brunborg, I. M. et al., 2004, supra; Dupont, K. et al., 2009, Transmission of different variants of PCV2 and viral dynamics in a research facility with pigs mingled from PMWS-affected herds and non-affected herds, Vet Microbiol 139:219-26; Fenaux, M. et al., 2004, supra; Harding, J. C et al., 2008, Porcine circovirus-2 DNA concentration distinguishes wasting from nonwasting pigs and is correlated with lesion distribution, severity, and nucleocapsid staining intensity, J Vet Diagn invest 20:274-82; Krakowka, S. et al., 2005, Features of porcine circovirus-2 disease: correlations between lesions, amount and distribution of virus, and clinical outcome, J Vet Diagn Invest 17:213-22; Mcintosh, K. A. et al., 2009, supra; Olvera, A. et al., 2004, supra; Yang, Z. Z. et al., 2007, supra).

After demonstrating that the chimeric PCV1-2b virus is attenuated in the susceptible and sensitive CD/CD pig model, the inventors then conducted a combined immunogenicity and challenge study in conventional SPF pigs. Three-week-old conventional cross-breed SPF pigs were chosen for the immunogenicity/challenge experiment in order to more closely mimic field vaccination conditions since such a live-attenuated vaccine will be eventually used in conventional pigs. Though clinical PCVAD was not expected in this conventional SPF model based on our earlier published studies (Fenaux, M. et al., 2002, supra; Fenaux, M. et al., 2004, supra; Fenaux, M. et al., 2004, supra; Fenaux, M. et al., 2003, supra, Fenaux, M. et al., 2004A. supra; Opriessnig, T, et al., 2009, Difference in severity of porcine circovirus type two-induced pathological lesions between Landrace and Pietrain pigs, J Anim Sci 87:1582-90; Opriessnig, T. et al., 2008, supra), it was anticipated that the level of viremia, viral loads and the characteristic histological lesions in lymphoid tissues induced by PCV2 in the conventional pig model are sufficient parameters for evaluating vaccine efficacy (Fenaux, M. et al., 2004, supra). As a live-attenuated vaccine, it is important to determine if chimeric PCV1-2b virus can induce sufficient level of protective antibody response upon vaccination of pigs. Two of the four currently available vaccines are based on recombinant PCV2a capsid proteins, and thus PCV2 capsid-specific humoral immune response is known to be important for protection. The results from the present invention showed that PCV2 capsid-specific antibodies were detected in the sera of PCV1-2b-vaccinated pigs as early as 14 dpv, and by 28 dpv all of the 20 vaccinated pigs had seroconverted to anti-PCV2 capsid-specific antibody. The antibody titers plateaued by 35 dpv and remained high at the time of challenge at 56 dpv, indicating that the chimeric PCV1-2b vaccine virus is capable of eliciting strong humoral immune response in conventional pigs.

Upon challenge with either wildtype PCV2a or PCV2b subtype, conventional SPF pigs vaccinated with the attenuated chimeric PCV1-2b virus had significantly lower viral DNA loads in the serum and TBLN tissues, significantly decreased level of severity and incidence of characteristic microscopic lesions, and significantly lower amounts of PCV2-specific antigen in lymphoid tissues compared to the unvaccinated controls, indicating that the chimeric PCV1-2b virus induced protective immunity against wildtype virus challenge. The results also showed that pigs vaccinated with the chimeric PCV1-2b virus were equally protected against homologous challenge with PCV2b subtype and heterologous challenge with the PCV2a subtype, as evidenced by the complete lack of PCV2a or PCV2b viremia, significant reductions in viral 7 loads in lymphoid tissues, and significantly lower overall lymphoid lesion scores in vaccinated pigs compared to unvaccinated controls, regardless of challenge virus subtype. Therefore, it appears that the new live-attenuated chimeric PCV1-2b vaccine candidate induces both protective and cross-protective immunity against both PCV2 subtypes.

Figure 5:
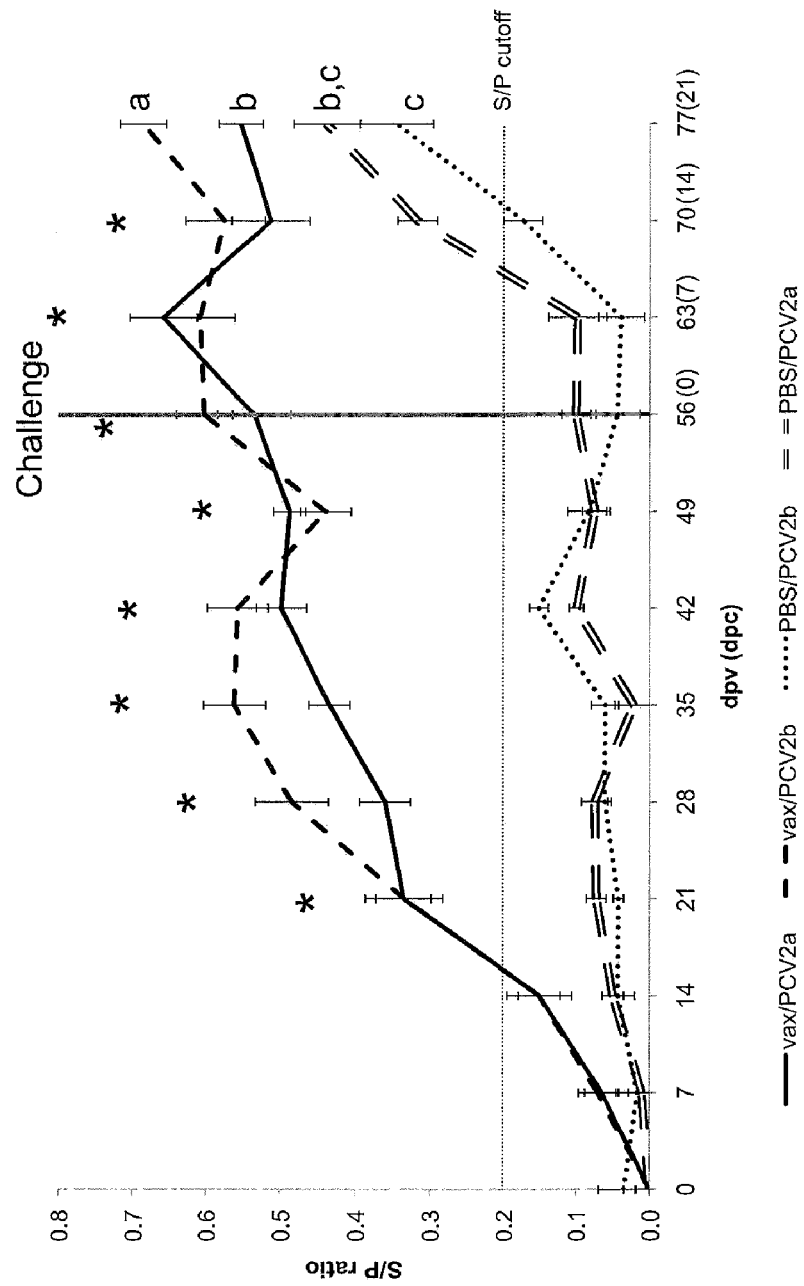

Some recent studies have reported that, in general, the PCV2b subtype is associated with more severe clinical disease when compared to the PCV2a subtype (Carman, S. et al., 2008, supra; Chae, J. S. and K. S. Choi, 2009, supra; Grau-Roma, L et al., 2008, A proposal on porcine circovirus type 2 (PCV2) genotype definition and their relation with postweaning muitisystemic wasting syndrome (PMWS) occurrence, Vet Microbiol 128:23-35). However, it remains debatable whether or not the PCV2b subtype is more virulent than the PCV2a subtype, since other studies could not definitively show a significant difference in virulence between PCV2a and PCV2b (An, D. J. et al., 2007, supra; Lager, K. M. et al., 2007, supra; Madson, D. M. et al., 2008, supra; Opreissnig, T. et al., 2006, supra; Opriessnig, T. et al., 2008, supra). Because of the sequence divergence between PCV2a and PCV2b, it is possible that the two subtypes of PCV2 may differ in pathogenicity since it has been shown that only two amino acid changes in the cap gene were sufficient to alter the pathogenicity of PCV2a (Fenaux, M. et al., 2004, Two amino acid mutations in the capsid protein of type 2 porcine circovirus (PCV2) enhanced PCV2 replication in vitro and attenuated the virus in vivo, J Viol 78:13440-6). In the unvaccinated control group in the current study, where half of the pigs were challenged with PCV2a or PCV2b, the inventors did not observe any significant difference in virulence between groups. The challenge doses for PCV2a and PCV2b were equivalent, but there was no significant difference in PCV2 viral loads in serum and TBLN tissues, the characteristic microscopic lesion scores, or the amounts of PCV2 antigen in lymphoid tissues between the PCV2a and PCV2b challenge groups. There were some minor differences in the antibody response, including a slightly delayed seroconversion to PCV2b compared to PCV2a in the unvaccinated pigs (FIG. 5). In the vaccinated pigs, PCV2b challenge resulted in slightly greater overall lymphoid lesion scores while the PCV2a challenge resulted in a higher number of TBLN tissues positive by qPCR. Overall, the results are consistent with other studies that have found no significant difference in PCV2a and PCV2b pathogenicity under experimental conditions (An, D. J. et al., 2007, supra; Lager, K. M et al., 2007, supra; Madson, D. M. et al., 2008, supra; Opriessnig, T. et al., 2006, supra; Opriessnig, T. et al., 2008, supra).

Differences in the antigenic profiles between PCV2a and PCV2b subtypes have been reported, and it has been speculated that a lack of sufficient level of cross-protection by the current PCV2a-based commercial vaccines may have contributed to an increase in PCVAD severity associated with the PCV2b subtype in global pig populations (Cheung, A. K. et al., 2007, supra; Dupont, K. et al., 2008, supra; Lekcharoensuk, P. et al., 2004, supra; Shang, S. B. et al., 2009, supra). Most of the sequence variations between PCV2a and PCV2b appear in the capsid gene, including a signature distinctive amino acid motif (Cheung, A. K. et al., 2007, supra; Olvera, A. et al., 2004, supra). Antibodies raised against this motif are capable of differentiating between PCV2a and PCV2b in vitro, indicating possible differences in antigenicity (Beach et al, unpublished data). The results from the present invention showed that a live-attenuated vaccine, PCV 1-2b, based on the capsid of the new PCV2b subtype does protect against heterologous challenge by PCV2a, thus supporting previous evidence of cross-protection of PCV2b subtype conferred by the PCV2a-based inactivated commercial vaccines (Fort, M., et al., 2008, supra; Fort, M. et al., 2009, supra; Opriessnig, T. et al., 2009, supra; Opriessnig, T. et al., 2008, supra).

In summary, the data from the present invention demonstrate that the chimeric PCV1-2b vaccine candidate based on the new PCV2b subtype is attenuated in CD/CD pigs and induces protective and cross-protective immunity in vaccinated conventional pigs against both PCV2b and PCV2a challenge, respectively. The results from the present invention will set the stage for further development of this chimeric PCV1-2b virus as the first live-attenuated vaccine against PCV2 infection and PCVAD. Although the PCV1-2b vaccine virus alone offered cross-protection against both PCV2a and PCV2b subtypes, it may be more advantageous in the future to combine the PCV1-2b vaccine from the present invention with the current PCV2a-based commercial vaccines for a more complete protection.

Vaccines of the infectious viral and molecular DNA clones, and methods of using them, are also included within the scope of the present invention. Inoculated pigs are protected from serious viral infection and other diseases caused by PCV2 infection or co-infection. The novel method protects pigs in need of protection against viral infection by administering to the pig an immunologically effective amount of a vaccine according to the invention, such as, for example, a vaccine comprising an immunogenic amount of the infectious PCV DNA, a plasmid or viral vector containing the infectious DNA clone of PCV, the recombinant PCV DNA, the polypeptide expression products, etc. Other antigens such as PRRSV, PPV, other infectious swine agents and immune stimulants may be given concurrently to the pig to provide a broad spectrum of protection against viral infections.

The vaccines comprise, for example, the infectious viral and molecular DNA clones, the cloned PCV infectious DNA genome in suitable plasmids or vectors such as, for example, the pSCK vector, an avirulent, live virus, an inactivated virus, etc. in combination with a nontoxic, physiologically acceptable carrier and, optionally, one or more adjuvants. The vaccine may also comprise the infectious PCV2 molecular DNA clone described herein. The infectious PCV DNA, the plasmid DNA containing the infectious viral genome and the live virus are preferred with the live virus being most preferred. The avirulent, live viral vaccine of the present invention provides an advantage over traditional viral vaccines that use either attenuated, live viruses which run the risk of reverting back to the virulent state or killed cell culture propagated whole virus which may not induce sufficient antibody immune response for protection against the viral disease.

Vaccines and methods of using them are also included within the scope of the present invention. Inoculated mammalian species are protected from serious viral infection, may also provide protection for disease related to co-infection of PCV, such as PCVAD and porcine dermatitis and nephropathy syndrome (PDNS), and other related illness. The vaccines comprise, for example, an inactivated or attenuated porcine TTV virus, a nontoxic, physiologically acceptable carrier and, optionally, one or more adjuvants.

The adjuvant, which may be administered in conjunction with the vaccine of the present invention, is a substance that increases the immunological response of the pig to the vaccine. The adjuvant may be administered at the same time and at the same site as the vaccine, or at a different time, for example, as a booster. Adjuvants also may advantageously be administered to the pig in a manner or at a site different from the manner or site in which the vaccine is administered. Suitable adjuvants include, but are not limited to, aluminum hydroxide (alum), immunostimulating complexes (ISCOMS), non-ionic block polymers or copolymers, cytokines (like IL-1, IL-2, IL-7, IFN-α, IFN-β, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

The vaccines may further contain additional antigens to promote the immunological activity of the infectious PCV DNA clones such as, for example, porcine reproductive and respiratory syndrome virus (PRRSV), porcine parvovirus (PPV), other infectious swine agents and immune stimulants.

The new vaccines of this invention are not restricted to any particular type or method of preparation. The cloned viral vaccines include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

As a further benefit, the preferred live virus of the present invention provides a genetically stable vaccine that is easier to make, store and deliver than other types of attenuated vaccines.

Another preferred vaccine of the present invention utilizes suitable plasmids for delivering the nonpathogenic DNA clone to pigs. In contrast to the traditional vaccine that uses live or killed cell culture propagated whole virus, this invention provides for the direct inoculation of pigs with the plasmid DNA containing the infectious viral genome.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective response in pigs (e.g., proteins derived from ORF3, ORF4, etc.). Such identified genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides (see, for instance, Zoller et al., DNA 3:479-488, 1984). An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

An immunologically effective amount of the vaccines of the present invention is administered to a pig in need of protection against viral infection. The immunologically effective amount or the immunogenic amount that inoculates the pig can be easily determined or readily titrated by routine testing. An effective amount is one in which a sufficient immunological response to the vaccine is attained to protect the pig exposed to the PCV virus. Preferably, the pig is protected to an extent in which one to all of the adverse physiological symptoms or effects of the viral disease are significantly reduced, ameliorated or totally prevented.

The vaccine can be administered in a single dose or in repeated doses. Dosages may range, for example, from about 1 microgram to about 1,000 micrograms of the plasmid DNA containing the infectious chimeric DNA genome (dependent upon the concentration of the immuno-active component of the vaccine), preferably 100 to 200 micrograms of the chimeric PCV1-2 DNA clone, but should not contain an amount of virus-based antigen sufficient to result in an adverse reaction or physiological symptoms of viral infection. Methods are known in the art for determining or titrating suitable dosages of active antigenic agent to find minimal effective dosages based on the weight of the pig, concentration of the antigen and other typical factors. Preferably, the infectious viral DNA clone is used as a vaccine, or a live infectious virus can be generated in vitro and then the live virus is used as a vaccine. In that case, from about 50 to about 10,000 of the 50% tissue culture infective dose ($TCID_{50}$) of live virus, for example, can be given to a pig.

The new vaccines of this invention are not restricted to any particular type or method of preparation. The vaccines include, but are not limited to, modified live vaccines, inactivated vaccines, subunit vaccines, attenuated vaccines, genetically engineered vaccines, etc.

The advantages of live vaccines are that all possible immune responses are activated in the recipient of the vaccine, including systemic, local, humoral and cell-mediated immune responses. The disadvantages of live virus vaccines, which may outweigh the advantages, lie in the potential for contamination with live adventitious viral agents or the risk that the virus may revert to virulence in the field.

To prepare inactivated. virus vaccines, for instance, the virus propagation and virus production can occur in cultured porcine cell lines such as, without limitation PK-15 cells, Serial virus inactivation is then optimized by protocols generally known to those of ordinary skill in the art or, preferably, by the methods described herein.

Inactivated virus vaccines may be prepared by treating the procine circovirus with inactivating agents such as formalin or hydrophobic solvents, acids, etc., by irradiation with ultraviolet light or X-rays, by heating, etc, Inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus. Inactivation by heating is conducted at a temperature and for a length of time sufficient to inactivate the virus. inactivation by inadiation is conducted using a wavelength of light or other energy source for a length of time sufficient to inactivate the virus. The virus is considered inactivated if it is unable to infect a cell susceptible to infection.

Genetically engineered vaccines, which are also desirable in the present invention, are produced by techniques known in the art. Such techniques involve, but are not limited to, the use of RNA, recombinant DNA, recombinant proteins, live viruses and the like.

For instance, after purification, the wild-type virus may be isolated from suitable clinical, biological samples such as serum, fecal, saliva, semen and tissue samples by methods known in the art, preferably by the method taught herein using infected pigs or infected suitable cell lines. The DNA is extracted from the biologically pure virus or infectious agent by methods known in the art, and purified by methods known in the art, preferably by ultracentrifugation in a CsCl gradient. The cDNA of viral genome is cloned into a suitable host by methods known in the art (see Maniatis et al., id.), and the virus genome is then analyzed to determine essential regions of the genome for producing antigenic portions of the virus. Thereafter, the procedure is generally the same as that for the modified live vaccine, an inactivated. vaccine or a subunit vaccine.

Genetically engineered vaccines based on recombinant DNA technology are made, for instance, by identifying the portion of the viral gene which encodes for proteins responsible for inducing a stronger immune or protective response in pigs (e.g., immunogenic viral protein such as capsid protein derived from ORF2). Such identified genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co. (1992)). The host cells are cultured, thus expressing the desired vaccine proteins, which can be purified to the desired extent and formulated into a suitable vaccine product.

Alternatively, DNA from the isolated porcine PCV which encode one or more capsid proteins can be inserted into live vectors, such as a poxvirus or an adenovirus and used as a vaccine.

An immunologically effective amount of the vaccine of the present invention is administered to an porcine or mammalian species in need of protection against said infection or syndrome. The "immunologically effective amount" can be easily determined or readily titrated by routine testing. An effective amount is one in which a sufficient immunological. response to the vaccine is attained. to protect the pig or other mammal exposed to the porcine TTV virus which may cause PCVAD, porcine dermatitis and nephropathy syndrome (PDNS), or related illness. Preferably, the pig or other mammalian species is protected to an extent in which one to all of the adverse physiological symptoms or effects of the viral disease are found to be significantly reduced, ameliorated or totally prevented.

The vaccine can be administered in a single dose or in repeated doses. Dosages may contain, for example, from 1 to 1,000 micrograms of virus-based antigen (dependent upon the concentration of the immuno-active component of the vaccine), but should not contain an amount of virus-based antigen sufficient to result in an adverse reaction or physiological symptoms of viral infection. Methods are known in the art for determining or titrating suitable dosages of active antigenic agent based on the weight of the bird or mammal, concentration of the antigen and other typical factors.

The vaccine can be administered to pigs. Also, the vaccine can be given to humans such as pig farmers who are at high risk of being infected by the viral agent. The vaccine can conveniently be administered. orally, intrabuccally, intranasally, transdermally, parenterally, etc. The parenteral route of administration includes, but is not limited to, intramuscular, intravenous, intraperitoneal and subcutaneous routes.

When administered as a liquid, the present vaccine may be prepared in the form of an aqueous solution, a syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions which contain suspending or emulsifying agents in combination with other standard co-formulants. These types of liquid formulations may be prepared by conventional methods, Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of mammalian body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives which can be employed in the present vaccine include, but are not limited to, dextrose, conventional antioxidants and conventional chelating agents such as ethylenediamine tetraacetic acid (EDTA). Parenteral dosage forms must also be sterilized prior to use.

TABLE 1

Oligonucleotide primers used in the construction of infectious DNA clones of PCV2b and chimeric PCV1-2b

| Primer | Sequence (5'-3') | Amplicon size (bp) |
|---|---|---|
| A | TTT CCG CGG GCT GGC TGA ACT TTT GAA AG | 1,779 |
| B | AGC CCG CGG AAA TTT CTG ACA AAC GTT AC | |
| C | CGT AAT GGT TTT TAT TTT TAA GGG TTA AGT GG | 718 |
| D | CTT TCA CTT TTA TAG GAT GAC GTA TCC AAG GAG G | |
| E | TTC GGG TAC CCG AAG GCC GAT T | 122 |
| F | CAC TTA ACC CTT AAA AAT AAA AAC CAT TAC GAT | |
| G | CCT CCT TGG ATA CGT CAT CCT ATA AAA GTG AAA G | 1,043 |
| H | CAG TGG ATC CCC CGG GCT GCA GGA | |

TABLE 2

Distribution of histopathological lesions in tissues of caesarean-derived colostrum-deprived (CD/CD) pigs experimentally inoculated with PBS buffer, PCV1-2b chimeric virus, and wildtype PCV2b virus

| | | | No. of pigs with lesions/no. examined (mean score) | | | | | | |
|---|---|---|---|---|---|---|---|---|---|
| dpi | Group | Inoculum | Lung | Liver | Thymus | Heart | Kidney | Ileum | Colon |
| 21/nec[a] | 1 | PBS | 3/5 (0.8) | 1/5 (0.4) | 0/5 | 0/5 | 0/5 | 0/5 | 0/5 |
| | 2 | PCV1-2b | 4/5 (1.0) | 3/5 (1.0) | 1/5 (0.2) | 0/5 | 2/5 (0.6) | 1/5 (0.2) | 0/5 |
| | 3 | PCV2b | 5/5 (2.8) | 5/5 (2.4) | 2/5 (0.6) | 1/5 (0.2) | 3/5 (0.8) | 4/5 (2.0) | 3/5 (1.0) |

TABLE 2-continued

Distribution of histopathological lesions in tissues of caesarean-derived colostrum-deprived (CD/CD) pigs experimentally inoculated with PBS buffer, PCV1-2b chimeric virus, and wildtype PCV2b virus

| | | | | | | | | |
|---|---|---|---|---|---|---|---|---|
| 42/nec[a] | 1 | PBS | 0/5 | 0/5[I] | 0/5 | 0/5 | 0/5[I] | 0/5 | 0/5 |
| | 2 | PCV1-2b | 4/5 (1.0) | 4/5 (0.8)[I,II] | 0/5 | 3/5 (0.6) | 3/5 (1.6)[I,II] | 1/5 (0.2) | 0/5 |
| | 3 | PCV2b | 3/5 (2.0) | 5/5 (1.4)[II] | 2/4[d] (0.75) | 1/5 (0.2) | 5/5 (2.6)[II] | 4/5 (1.6) | 4/5 (1.0) |

| | | | No. of pigs with lesions/no. examined (mean score) | | | | | |
|---|---|---|---|---|---|---|---|---|
| | | | Lymph nodes | | Spleen | | Tonsil | |
| dpi | Group | Inoculum | LD[b] | HR[c] | LD[b] | HR[c] | LD[b] | HR[c] |
| 21/nec[a] | 1 | PBS | 1/5 (0.2)[I] | 0/5[I] | 0/5 | 0/5 | 0/5[I] | 0/5[I] |
| | 2 | PCV1-2b | 2/5 (0.6)[I,II] | 1/5 (0.4)[I,II] | 1/5 (0.2) | 1/5 (0.2) | 1/5 (0.2)[I,II] | 1/5 (0.4)[I,II] |
| | 3 | PCV2b | 5/5 (2.6)[II] | 5/5 (2.2)[II] | 4/5 (2.0) | 4/5 (1.8) | 5/5 (2.4)[II] | 5/5 (2.2)[II] |
| 42/nec[a] | 1 | PBS | 0/5[I] | 0/5 | 0/5 | 0/5 | 0/5 | 0/5 |
| | 2 | PCV1-2b | 2/5 (0.4)[I,II] | 1/5 (0.4) | 0/5 | 0/5 | 1/5 (0.2) | 1/5 (0.2) |
| | 3 | PCV2b | 5/5 (2.2)[II] | 4/5 (2.0) | 3/5 (1.2) | 3/5 (1.0) | 4/5 (2.0) | 3/5 (1.8) |

[a]pigs that died or were euthanized early due to PCVAD were included in the analysis
[b]lymphoid depletion
[c]histiocytic replacement
[d]thymus was not present in one of the pigs tested
[I,II]groups that have statistically significant differences in group median score have different numerals

TABLE 3

Immunohistochemical detection of PCV2 capsid-specific antigen in caesarean-derived colostrum-deprived (CD/CD) experimentally inoculated with PBS buffer, PCV1-2b chimeric virus, and PCV2b wildtype virus

| | | | No. of pigs positive/no. tested (mean score) | | | | | | | | | |
|---|---|---|---|---|---|---|---|---|---|---|---|---|
| dpi | Group | Inoculum | Lung | Liver | Thymus | Heart | Kidney | Ileum | Colon | Lymph nodes | Spleen | Tonsil |
| 21/nec[a] | 1 | PBS | 0/5[I] | 0/5[I] | 0/5 | 0/5 | 0/5 | 0/5 | 0/5 | 0/5[I] | 0/5 | 0/5[I] |
| | 2 | PCV1-2b | 0/5[I] | 1/5 (0.2)[I,II] | 1/5 (0.2) | 0/5 | 1/5 (0.2) | 1/5 (0.2) | 1/5 (0.2) | 1/5 (0.4)[I,II] | 1/5 (0.2) | 4/5 (1.0)[I,II] |
| | 3 | PCV2b | 5/5 (1.6)[II] | 5/5 (1.4)[II] | 4/5 (1.6) | 1/5 (0.2) | 2/5 (0.4) | 4/5 (2.0) | 3/5 (1.6) | 5/5 (2.2)[II] | 4/5 (1.6) | 5/5 (2.4)[II] |
| 42/nec[a] | 1 | PBS | 0/5 | 0/5 | 0/5 | 0/5 | 0/5 | 0/5 | 1/5 (0.2) | 0/5[I] | 0/5 | 0/5[I] |
| | 2 | PCV1-2b | 0/5 | 0/5 | 0/5 | 0/5 | 1/5 (0.2) | 0/5 | 0/5 | 4/5 (0.8)[I,II] | 1/5 (0.2) | 1/5 (0.2)[I,II] |
| | 3 | PCV2b | 3/5 (1.6) | 3/5 (1.4) | 2/4[b] (1.5) | 1/5 (0.2) | 4/5 (1.8) | 4/5 (1.8) | 3/5 (1.2) | 5/5 (2.2)[II] | 3/5 (1.4) | 5/5 (2.2)[II] |

[a]Pigs that died or were euthanized early due to PCVAD were included in the analysis
[b]thymus was not present in one of the pigs tested
[I,II]groups that have statistically significant differences in group median score have different numerals

TABLE 4

Microscopic lesions and PCV2-specific antigen in lymphoid tissues during necropsy in conventional pigs vaccinated with PBS buffer or chimeric PCV1-2b candidate vaccine and subsequently challenged with PCV2a or PCV2b wildtype viruses

| | | | No. of pigs with lesions/no. examined (mean score) | | | | | | | | |
|---|---|---|---|---|---|---|---|---|---|---|---|
| | Inoculum | Challenge | Lymph nodes | | | Spleen | | | Tonsil | | |
| Group | (0 dpv) | (56 dpv) | LD[a] | HR[b] | IHC[c] | LD[a] | HR[b] | IHC[c] | LD[a] | HR[b] | IHC[c] |
| 1 | PCV1-2b | PCV2b | 8/10 (0.9)[I] | 3/10 (0.3)[I] | 2/10 (0.2) | 7/10 (0.7) | 5/10 (0.5) | 1/10 (0.1) | 2/10 (0.2) | 0/10 | 0/10 |
| 2 | PBS | PCV2b | 9/9 (1.7)[II] | 9/9 (1.6)[II] | 6/9 (0.8) | 5/9 (0.6) | 2/9 (0.3) | 0/9 | 0/9 | 0/9 | 1/9 (0.1) |
| 3 | PCV1-2b | PCV2a-40895 | 0/10[I] | 0/10 | 0/10[I] | 0/10[I] | 0/10 | 0/10 | 0/10 | 1/10 (0.1) | 0/10 |
| 4 | PBS | PCV2a-40895 | 9/10 (1.1)[II] | 3/10 (0.4) | 7/10 (1.1)[II] | 6/10 (0.6)[II] | 0/10 | 0/10 | 2/10 (0.2) | 0/10 | 4/10 (0.4) |

[a]lymphoid depletion
[b]histiocytic replacement
[c]detection of PCV2-specific antigen by immunohistochemistry (IHC); no. of pigs with positive IHC/no. examined (mean IHC antigen score)
[I,II]pairs of treatments that have statistically significant differences in group median score have different numerals

What is claimed is:

1. A chimeric PCV1-2b virus comprising a recombinant PCV1 that encodes the capsid protein of PCV2b subtype in place of the capsid protein of PCV1, wherein the capsid protein of the PCV2b subtype is encoded by the ORF2 capsid gene of a wild-type PCV2b strain having the full-length genomic nucleotide sequence set forth in SEQ ID NO: 2.

2. The chimeric PCV1-2b virus set forth in claim 1, wherein the chimeric PCV1-2b virus is an inactivated chimeric PCV1-2b virus.

3. The chimeric PCV1-2b virus set forth in claim 1, wherein the chimeric PCV1-2b virus is a live chimeric PCV1-2b virus.

4. A viral vaccine comprising a physiologically acceptable carrier and an immunogenic amount of a chimeric PCV1-2b virus which comprises a recombinant PCV1 that encodes the capsid protein of PCV2b subtype in place of the capsid protein of PCV1, wherein the capsid protein of the PCV2b subtype is encoded by the ORF2 capsid gene of a wild-type PCV2b strain having the full-length genomic nucleotide sequence set forth in SEQ ID NO: 2.

5. The viral vaccine according to claim 4, wherein the vaccine contains live chimeric PCV1-2b virus.

6. The viral vaccine according to claim 4, wherein the vaccine contains inactivated chimeric PCV1-2b virus.

7. The viral vaccine according to claim 4, wherein the vaccine further contains an adjuvant.

8. The viral vaccine according to claim 4, wherein the vaccine protects against PCV2a and PCV2b infection.

9. A method of immunizing a pig against PCV2 viral infection, comprising administering to a pig an immunologically effective amount of the vaccine according to claim 4.

10. The method according to claim 9, comprising administering a live chimeric PCV1-2b virus to the pig.

11. The method according to claim 9, comprising administering an inactivated chimeric PCV1-2b virus to the pig.

12. The method according to claim 9, comprising administering the vaccine parenterally, intranasally, intradermally, or transdermally to the pig.

13. The method according to claim 9, comprising administering the vaccine intralymphoidly or intramuscularly to the pig.

14. A method of protecting a pig against porcine circovirus-associated disease (PCVAD), comprising administering to a pig an immunologically effective amount of the vaccine according to claim 4.

* * * * *

UNITED STATES PATENT AND TRADEMARK OFFICE

(12)            CERTIFICATE EXTENDING PATENT TERM
UNDER 35 U.S.C. § 156

| | | | |
|---|---|---|---|
| (68) | PATENT NO. | : | 9,585,951 |
| (45) | ISSUED | : | March 7, 2017 |
| (75) | INVENTOR | : | Meng et al. |
| (73) | PATENT OWNER | : | Virginia Tech Intellectual Properties, Inc. |
| (95) | PRODUCT | : | Fostera® Gold PCV MH |

This is to certify that an application under 35 U.S.C. § 156 has been filed in the United States Patent and Trademark Office, requesting extension of the term of U.S. Patent No. 9,585,951 based upon the regulatory review of the product Fostera® Gold PCV MH by the United States Department of Agriculture. According to United States Patent and Trademark Office records, the original expiration date of the patent as of the date of issuance of this certificate is January 29, 2023. Because it appears that the requirements of the law have been met, this certificate extends the term of the patent for the period of

(94)                               331 days subject to the payment of maintenance fees as provided by law, with all rights pertaining thereto as provided by 35 U.S.C. § 156.

I have caused the seal of the United States Patent and Trademark Office to be affixed this 7th day of August 2020.

Andrei Iancu
Under Secretary of Commerce for Intellectual Property and
  Director of the United States Patent and Trademark Office